(12) United States Patent
Peterson et al.

(10) Patent No.: US 7,112,214 B2
(45) Date of Patent: Sep. 26, 2006

(54) DYNAMIC BIOABSORBABLE FASTENER FOR USE IN WOUND CLOSURE

(75) Inventors: James A. Peterson, Edina, MN (US); Christopher J. Sperry, Plymouth, MN (US); Joseph M. Gryskiewicz, Edina, MN (US); Delmer L. Smith, Edina, MN (US)

(73) Assignee: Incisive Surgical, Inc., Minnetonka, MN (US)

( * ) Notice: Subject to any disclaimer, the term of this patent is extended or adjusted under 35 U.S.C. 154(b) by 177 days.

(21) Appl. No.: 10/603,397

(22) Filed: Jun. 25, 2003

(65) Prior Publication Data
US 2004/0059378 A1  Mar. 25, 2004

Related U.S. Application Data

(60) Continuation of application No. 10/603,397, filed on Jun. 25, 2003, and a continuation-in-part of application No. 10/448,838, filed on May 30, 2003, which is a division of application No. 10/179,628, filed on Jun. 25, 2002, now Pat. No. 6,726,705.

(51) Int. Cl.
*A61B 17/08* (2006.01)
*A61D 1/00* (2006.01)
*A61B 17/10* (2006.01)

(52) U.S. Cl. .................. 606/220; 606/75; 606/142; 606/151; 606/219

(58) Field of Classification Search .............. 606/75, 606/151, 213, 215, 219, 220, 154, 157; 411/457, 411/458, 460, 461
See application file for complete search history.

(56) References Cited

U.S. PATENT DOCUMENTS 718,649 A * 1/1903 Morehouse ................. 411/461

(Continued)

FOREIGN PATENT DOCUMENTS

EP        1 323 384 A2    7/2003

(Continued)

OTHER PUBLICATIONS

Brochure: *Information Booklet for Auto Suture® Purse String Instrument*, Auto Suture Company, a division of United States Surgical Corporation, Norwalk, CT, 2 pgs., 1978.

(Continued)

*Primary Examiner*—Gleen K. Dawson
*Assistant Examiner*—Michael G. Mendoza
(74) *Attorney, Agent, or Firm*—Patterson, Thuente, Skaar & Christensen, P.A.

(57) ABSTRACT

A fastener for insertion into pierced openings of a tissue wound has a body formed of a generally bioabsorbable polymer defining an initial capture area internal to the body. The body includes a pair of arms, each with an inwardly projecting cleat operably joined at an elbow portion defining an internal elbow angle. The arms are operably joined to a backspan at a shoulder portion defining an internal shoulder angle. A durable tissue retention zone is defined between the cleat and the arm. The elbow portion and the internal elbow angle define an insertion width greater than a width of the pierced openings resulting in the pierced openings stretching over the cleat and being elastically retained within the durable tissue retention zone. The fastener initially captures wound tissue in the initial capture area and then dynamically reforms in response to lateral stresses applied by the wound tissue without a fracture failure of the fastener until a minimum degradation period.

11 Claims, 32 Drawing Sheets

U.S. PATENT DOCUMENTS

| | | | |
|---|---|---|---|
| 2,283,814 A * | 5/1942 | La Place | 29/432 |
| 2,351,608 A | 6/1944 | Greenwood | |
| 2,439,383 A | 4/1948 | Erickson | |
| 2,526,902 A | 10/1950 | Rublee | |
| 2,881,762 A | 4/1959 | Lowrie | |
| 2,959,172 A | 11/1960 | Held | |
| 3,082,426 A | 3/1963 | Miles | |
| 3,123,077 A | 3/1964 | Alcamo | |
| 3,297,033 A | 1/1967 | Schmitt et al. | |
| 3,344,790 A | 10/1967 | Dorner | |
| 3,636,956 A | 1/1972 | Schneider | |
| 3,643,851 A | 2/1972 | Green et al. | |
| 3,716,058 A | 2/1973 | Tanner, Jr. | |
| 3,757,629 A * | 9/1973 | Schneider | 411/443 |
| 3,792,010 A | 2/1974 | Wasserman et al. | |
| 4,014,492 A | 3/1977 | Rothfuss | |
| 4,027,676 A | 6/1977 | Mattei | |
| 4,047,533 A | 9/1977 | Perciaccante et al. | |
| 4,162,678 A | 7/1979 | Fedotov et al. | |
| 4,259,959 A | 4/1981 | Walker | |
| 4,261,244 A | 4/1981 | Becht et al. | |
| 4,317,451 A | 3/1982 | Cerwin et al. | |
| 4,396,139 A | 8/1983 | Hall et al. | |
| 4,399,810 A | 8/1983 | Samuels et al. | |
| 4,407,286 A | 10/1983 | Noiles et al. | |
| 4,410,125 A | 10/1983 | Noiles et al. | |
| 4,428,376 A | 1/1984 | Mericle | |
| 4,430,998 A | 2/1984 | Harvey et al. | |
| 4,434,796 A | 3/1984 | Karapetian et al. | |
| 4,454,875 A * | 6/1984 | Pratt et al. | 606/75 |
| 4,467,805 A | 8/1984 | Fukuda | |
| 4,485,816 A | 12/1984 | Krumme | |
| 4,485,953 A | 12/1984 | Rothfuss | |
| 4,493,322 A | 1/1985 | Becht | |
| 4,505,273 A | 3/1985 | Braun et al. | |
| 4,506,669 A | 3/1985 | Blake, III | |
| 4,508,253 A | 4/1985 | Green | |
| 4,526,173 A | 7/1985 | Sheehan | |
| 4,526,174 A | 7/1985 | Froehlich | |
| 4,534,352 A * | 8/1985 | Korthoff | 606/220 |
| 4,535,772 A | 8/1985 | Sheehan | |
| 4,548,202 A | 10/1985 | Duncan | |
| 4,557,265 A | 12/1985 | Andersson | |
| 4,566,620 A | 1/1986 | Green et al. | |
| 4,568,009 A | 2/1986 | Green | |
| 4,570,623 A | 2/1986 | Ellison et al. | |
| 4,573,622 A | 3/1986 | Green et al. | |
| 4,583,670 A | 4/1986 | Alvarado | |
| 4,592,498 A | 6/1986 | Braun et al. | |
| 4,593,843 A | 6/1986 | Saravis | |
| 4,596,350 A | 6/1986 | Smith et al. | |
| 4,607,638 A | 8/1986 | Crainich | |
| 4,610,251 A | 9/1986 | Kumar | |
| 4,618,086 A | 10/1986 | Li et al. | |
| 4,619,262 A | 10/1986 | Taylor | |
| 4,637,380 A | 1/1987 | Orejola | |
| 4,646,741 A * | 3/1987 | Smith | 606/220 |
| 4,655,222 A | 4/1987 | Florez et al. | |
| 4,665,916 A | 5/1987 | Green | |
| 4,671,279 A | 6/1987 | Hill | |
| 4,676,245 A | 6/1987 | Fukuda | |
| 4,719,917 A | 1/1988 | Barrows et al. | |
| 4,728,020 A | 3/1988 | Green et al. | |
| 4,741,337 A | 5/1988 | Smith et al. | |
| 4,752,024 A | 6/1988 | Green et al. | |
| 4,753,636 A | 6/1988 | Free | |
| 4,762,260 A | 8/1988 | Richards et al. | |
| 4,776,506 A | 10/1988 | Green | |
| 4,789,090 A | 12/1988 | Blake, III | |
| 4,802,478 A | 2/1989 | Powell | |
| 4,887,601 A | 12/1989 | Richards | |
| 4,895,148 A | 1/1990 | Bays et al. | |
| 4,899,745 A | 2/1990 | Laboureau et al. | |
| 4,915,100 A | 4/1990 | Green | |
| 4,924,866 A | 5/1990 | Yoon | |
| 4,955,898 A | 9/1990 | Matsutani et al. | |
| 4,969,591 A | 11/1990 | Richards et al. | |
| 4,976,686 A | 12/1990 | Ball et al. | |
| 4,976,715 A | 12/1990 | Bays et al. | |
| 4,994,073 A | 2/1991 | Green | |
| 5,002,562 A | 3/1991 | Oberlander | |
| 5,007,921 A | 4/1991 | Brown | |
| 5,015,252 A | 5/1991 | Jones | |
| 5,026,390 A | 6/1991 | Brown | |
| 5,035,692 A | 7/1991 | Lyon et al. | |
| 5,044,540 A * | 9/1991 | Dulebohn | 227/175.1 |
| 5,047,047 A | 9/1991 | Yoon | |
| 5,058,315 A * | 10/1991 | Wagner | 47/1.01 R |
| 5,062,563 A | 11/1991 | Green et al. | |
| 5,078,731 A | 1/1992 | Hayhurst | |
| 5,089,009 A | 2/1992 | Green | |
| 5,108,422 A | 4/1992 | Green et al. | |
| 5,129,570 A | 7/1992 | Schulze et al. | |
| 5,156,609 A | 10/1992 | Nakao et al. | |
| 5,158,566 A | 10/1992 | Pianetti | |
| 5,158,567 A | 10/1992 | Green | |
| 5,160,339 A | 11/1992 | Chen et al. | |
| 5,179,964 A | 1/1993 | Cook | |
| 5,211,644 A | 5/1993 | VanBeek et al. | |
| 5,211,722 A * | 5/1993 | Wagner | 47/58.1 R |
| 5,236,440 A | 8/1993 | Hlavacek | |
| 5,242,457 A | 9/1993 | Akopov et al. | |
| 5,257,713 A | 11/1993 | Green et al. | |
| 5,258,009 A | 11/1993 | Conners | |
| 5,258,010 A | 11/1993 | Green et al. | |
| 5,258,012 A * | 11/1993 | Luscombe et al. | 606/220 |
| 5,263,973 A | 11/1993 | Cook | |
| 5,269,783 A | 12/1993 | Sander | |
| 5,269,792 A | 12/1993 | Kovac et al. | |
| 5,285,944 A | 2/1994 | Green et al. | |
| 5,292,326 A | 3/1994 | Green et al. | |
| 5,293,881 A * | 3/1994 | Green et al. | 128/898 |
| 5,297,714 A | 3/1994 | Kramer | |
| 5,304,204 A | 4/1994 | Bregen | |
| 5,324,307 A | 6/1994 | Jarrett et al. | |
| 5,333,772 A | 8/1994 | Rothfuss et al. | |
| 5,337,937 A | 8/1994 | Remiszewski et al. | |
| 5,342,376 A | 8/1994 | Ruff | |
| 5,350,400 A | 9/1994 | Esposito et al. | |
| 5,364,003 A | 11/1994 | Williamson, IV | |
| 5,366,134 A | 11/1994 | Green et al. | |
| 5,389,102 A | 2/1995 | Green et al. | |
| 5,392,979 A | 2/1995 | Green et al. | |
| 5,398,861 A | 3/1995 | Green | |
| D357,316 S | 4/1995 | Green et al. | |
| 5,413,584 A | 5/1995 | Schulze | |
| 5,415,334 A | 5/1995 | Williamson, IV et al. | |
| 5,417,361 A | 5/1995 | Williamson, IV | |
| 5,423,856 A | 6/1995 | Green | |
| 5,456,400 A * | 10/1995 | Shichman et al. | 227/176.1 |
| 5,456,401 A | 10/1995 | Green et al. | |
| 5,478,003 A | 12/1995 | Green et al. | |
| 5,480,089 A | 1/1996 | Blewett | |
| 5,482,197 A | 1/1996 | Green et al. | |
| 5,489,058 A | 2/1996 | Plyley et al. | |
| 5,489,287 A | 2/1996 | Green et al. | |
| 5,505,363 A | 4/1996 | Green et al. | |
| 5,509,596 A | 4/1996 | Green et al. | |
| 5,514,149 A | 5/1996 | Green et al. | |
| 5,542,594 A | 8/1996 | McKean et al. | |
| 5,544,802 A | 8/1996 | Crainich | |
| 5,549,619 A | 8/1996 | Peters et al. | |
| 5,551,622 A | 9/1996 | Yoon | |
| 5,558,266 A | 9/1996 | Green et al. | |

| | | |
|---|---|---|
| 5,562,241 A | 10/1996 | Knodel et al. |
| 5,571,285 A | 11/1996 | Chow et al. |
| 5,573,541 A | 11/1996 | Green et al. |
| 5,579,978 A | 12/1996 | Green et al. |
| 5,584,859 A | 12/1996 | Brotz |
| 5,591,178 A | 1/1997 | Green et al. |
| 5,593,423 A | 1/1997 | Person et al. |
| 5,618,311 A | 4/1997 | Gryskiewicz |
| 5,645,567 A | 7/1997 | Crainich |
| 5,658,312 A | 8/1997 | Green et al. |
| 5,662,258 A | 9/1997 | Knodel et al. |
| 5,662,655 A * | 9/1997 | Laboureau et al. ............ 606/75 |
| 5,667,527 A | 9/1997 | Cook |
| 5,706,997 A | 1/1998 | Green et al. |
| 5,725,538 A | 3/1998 | Green et al. |
| 5,725,554 A | 3/1998 | Simon et al. |
| 5,728,108 A | 3/1998 | Griffiths et al. |
| 5,794,834 A | 8/1998 | Hamblin et al. |
| 5,816,471 A | 10/1998 | Plyley et al. |
| 5,829,662 A | 11/1998 | Allen et al. |
| 5,843,084 A | 12/1998 | Hart et al. |
| 5,871,135 A | 2/1999 | Williamson, IV et al. |
| 5,878,937 A | 3/1999 | Green et al. |
| 5,902,319 A | 5/1999 | Daley |
| 5,908,427 A | 6/1999 | McKean et al. |
| 5,947,999 A * | 9/1999 | Groiso ....................... 606/219 |
| 5,964,774 A | 10/1999 | McKean et al. |
| 5,976,160 A | 11/1999 | Crainich |
| 5,984,949 A | 11/1999 | Levin |
| 5,993,476 A * | 11/1999 | Groiso ....................... 606/219 |
| 6,045,560 A | 4/2000 | McKean et al. |
| 6,083,242 A | 7/2000 | Cook |
| 6,090,131 A | 7/2000 | Daley |
| 6,120,526 A | 9/2000 | Daley |
| 6,131,789 A | 10/2000 | Schulze et al. |
| 6,149,658 A | 11/2000 | Gardiner et al. |
| 6,159,224 A | 12/2000 | Yoon |
| 6,241,747 B1 | 6/2001 | Ruff |
| 6,250,532 B1 | 6/2001 | Green et al. |
| 6,270,517 B1 | 8/2001 | Brotz |
| 6,325,805 B1 * | 12/2001 | Ogilvie et al. ................ 606/75 |
| 6,387,104 B1 | 5/2002 | Pugsley et al. |
| 6,387,113 B1 * | 5/2002 | Hawkins et al. ............ 606/219 |
| 6,409,743 B1 | 6/2002 | Fenton, Jr. |
| 6,423,088 B1 | 7/2002 | Fenton, Jr. |
| 6,599,310 B1 | 7/2003 | Leung et al. |
| 6,619,529 B1 | 9/2003 | Green et al. |
| 6,626,916 B1 | 9/2003 | Yeung et al. |
| 6,629,988 B1 | 10/2003 | Weadock |
| 6,638,297 B1 | 10/2003 | Huitema |
| 6,666,872 B1 | 12/2003 | Barreiro et al. |
| 6,767,356 B1 | 7/2004 | Kanner et al. |
| 6,773,437 B1 * | 8/2004 | Ogilvie et al. ................ 606/75 |
| 2002/0007184 A1 * | 1/2002 | Ogilvie et al. ................ 606/61 |
| 2002/0019636 A1 * | 2/2002 | Ogilvie et al. ................ 606/75 |
| 2002/0133181 A1 | 9/2002 | Tong |
| 2003/0028218 A1 | 2/2003 | Bauer |
| 2003/0139746 A1 * | 7/2003 | Groiso ........................ 606/75 |

FOREIGN PATENT DOCUMENTS

| | | | |
|---|---|---|---|
| FR | 2549544 | * | 1/1985 |
| JP | 06233772 | * | 1/2002 |

OTHER PUBLICATIONS

Brochure: *La Sutura Perde il Filo*, Farmitalia Carlo Erba, 4 pgs., not dated.

*Evaluation of New Absorbable Lactomer Subcuticular Staple*, G.C. Zachmann, P.A. Foresman, T.J. Bill, D.J. Bentrem, G.T. Rodeheaver, R.F. Edlich, Journal of Applied Biomaterial, vol. 5, No. 3, pp. 221-116, 1994.

* cited by examiner

DYNAMIC BIOABSORBABLE FASTENER FOR USE IN WOUND CLOSURE

RELATED APPLICATIONS AND PRIORITY CLAIM

The present application is a continuation application of co-pending U.S. patent application Ser. No. 10/603,397, filed Jun. 25, 2003, entitled "DYNAMIC BIOABSORBABLE FASTENER FOR USE IN WOUND CLOSURE," which is a Continuation-in-Part of U.S. patent application Ser. No. 10/179,628, filed Jun. 25, 2002, now allowed in U.S. Pat. No. 6,726,705, entitled, "MECHANICAL METHOD AND APPARATUS FOR BILATERAL TISSUE FASTENING," and co-pending U.S. Divisional application Ser. No. 10/448,838, filed May 30, 2003, entitled "MECHANICAL METHOD AND APPARATUS FOR BILATERAL TISSUE FASTENING," all of which are herein incorporated by reference in their entirety.

FIELD OF THE INVENTION

The present invention relates generally to the field of surgical fasteners for use in wound closure. More particularly, the present invention relates to a design for a dynamic, bioabsorbable fastener designed for through-and-through insertion across a wound having a capacity to reform when exposed to wound stresses greater than the initial static strength of the fastener while continuously retaining and approximating opposing sides of a wound during the healing process.

BACKGROUND OF THE INVENTION

When an opening in tissue is created either through an intentional incision or an accidental wound or laceration, biological healing of the opening commences through the proximity of the opposed living tissue surfaces. If the opening is very large or if its location subjects the wound to continual movement, a physician will seek to forcibly hold the sides of the opening together so as to promote the healing process.

In the case of skin tissue, for example, healing occurs best when the opposing dermal layers of the skin tissue are held in tight, primary proximity with each other. Human skin tissue is comprised of three distinct layers of tissue. The epidermal layer, also known as the epidermis, is the outermost layer and includes non-living tissue cells. The dermal layer, or dermis, is the middle layer directly below the epidermal layer and comprises the living tissue of the skin that is the strongest of the three layers. The subcutaneous, or hypodermis layer, is the bottom layer of skin tissue and includes less connective tissue, making this the weakest layer of skin tissue.

The most prevalent method for forcibly closing a tissue opening is through the use of a suture or "stitches." As early as the second century, the Greeks were using sutures to physically close skin openings. In its simplest form, a suture is simply a length of material that is attached to a tissue-piercing device, such as a needle, and looped through the opposing sides of a tissue opening. The suture is then pulled tight and the loop closes, causing the opposing sides of the tissue opening to come into close physical contact. The suture loop is held tight by the tying of a knot, or knots, or some other locking mechanism. The first sutures were made of animal gut. Eventually other natural suture materials including leather, horsehair, flax, cotton and silk came into use. As the sciences of medical and materials technology have advanced over the course of the past century, new bioabsorbable materials have been developed to further improve upon the basic suturing concept.

While traditional suturing remains a popular method of effectuating closure of skin openings, the use of fasteners, for example staples and staplers, as a skin closure technique has become increasingly popular, especially in surgical settings where the opening is created through a purposeful incision. In these settings, the incision tends to make a clean, straight cut with the opposing sides of the incision having consistent and non-jagged surfaces. Typically, stapling of a skin opening, for example, is accomplished by manually approximating the opposing sides of the skin opening and then positioning the stapler so that a staple will span the opening. The stapler is then manipulated such that the staple is driven into the skin with one leg being driven into each side of the skin opening and the cross-member of the staple traversing the skin opening. Generally, the staple is made of a deformable material such as surgical stainless steel and the legs of the staple are driven into an anvil causing the staple to deform so as to retain the skin tissue in a compressed manner within the staple. This process can be repeated along the length of the opening such that the entire incision is held closed during the healing process.

The earliest medical staple designs were manufactured of metal and designed to deform around the captured tissue. Examples of these staples include U.S. Pat. Nos. 2,684,070, 3,273,562 and 4,485,816. Although effective, metal staples suffer from the drawback of requiring post-operative removal. As the science of medical polymers developed, staple designs incorporating bioabsorbable materials became available. The use of these bioabsorbable materials eliminated the need for post-operative removal of the staples. Examples of these staples include U.S. Pat. Nos. 4,317,451, 4,741,337, 4,839,130 and 4,950,258. Due to the nature of bioabsorbable polymers; however, bioabsorbable staples could not be inserted with the same deformation approach used by metal staples. In fact, bioabsorbable staples were purposefully designed to avoid any deformation requirement, as deformation was seen as a potential failure mechanism. An example of such a design is illustrated by the inwardly biased skin fastener of U.S. Pat. No. 5,089,009. Thus, as the physical and chemical properties of bioabsorbable surgical staples evolved, the development of designs and insertion methods associated with bioabsorbable staples have focused on avoiding deformation of the bioabsorbable fastener.

One potential use for bioabsorbable fasteners is in the subcuticular application of such fasteners for use in closing skin wounds as shown, for example in a series of patents to Green et al. in U.S. Pat. Nos. 5,292,326, 5,389,102, 5,423,856, 5,489,287 and 5,573,541. These patents disclose the use of a bioabsorbable, rod-like fastener inserted in a subcuticular manner to assist the healing process. Another bioabsorbable fastener design contemplated for subcuticular wound closure is U.S. Pat. No. 5,618,311 to Gryskiewicz, in which a more traditional staple design is promoted.

If they could effectively retain tissue, the bioabsorbable staples of these designs would have many advantages over conventional metal staples, such as no visible scarring and no need for subsequent removal by a physician. Unfortunately, none of the designs for bioabsorbable staples to date has been incorporated into a medically or commercially efficacious fastener. It would be desirable to provide a bioabsorbable fastener for use in wound closure that could achieve the advantages of a bioabsorbable material and still provide for an efficacious wound closure.

SUMMARY OF THE INVENTION

The present invention is a bioabsorbable fastener for insertion into pierced openings on opposed sides of a tissue wound. A fastener body is formed of a generally bioabsorbable polymer material and defines an initial tissue capture zone internal to the fastener body. The fastener body includes a pair of fastener arms, a cleat operably joined to each fastener arm at an elbow portion and a backspan operably joined to each fastener arm at a shoulder portion. Each fastener arm is insertable into one of the pierced openings. Each cleat projects backward into the initial tissue capture zone with an internal elbow angle defined between the cleat and the fastener arm. A durable tissue retention zone of each fastener arm is defined between the cleat and the fastener arm. Each fastener arm has a maximum insertion width defined between outermost surfaces of the cleat and the fastener arm. Corresponding internal shoulder angles are defined between the backspan and each fastener arm and an internal midspan angle is defined between a midpoint of the backspan and the apex of each durable tissue retention zone.

The elbow portion and the internal elbow angle of each fastener arm are constructed with the maximum insertion width being greater than a width of the corresponding pierced opening such that at least a portion of the tissue surrounding the pierced opening is stretched over the cleat and elastically retained in the durable tissue retention zone for longer than a minimum degradation period of the bioabsorbable polymer material. The shoulder portions and the internal shoulder angles are constructed so as to capture wound tissue within the initial tissue capture zone during deployment of the fastener and then dynamically reform in response to lateral stresses applied by the wound tissue after deployment such that a sum of the internal elbow angles and the internal midspan angle remains less than 360 degrees without a fracture failure of the bioabsorbable polymer material until the minimum degradation period of the bioabsorbable polymer material.

While the use of bioabsorbable materials for a tissue fastener offers many advantages, the present invention is the first to recognize that the effective use of bioabsorbable materials in the design of a surgical fastener must both understand and overcome a number of issues related to the nature of bioabsorbable materials and human tissue, as well as the dynamic process of tissue healing.

First, the thermoplastic polymers used in typical bioabsorbable staples possess a viscoelastic quality or polymer creep when subjected to continuous stress loading due to the nature of their molecular level bonding and entanglements. Traditionally, bioabsorbable fastener designs have compensated for this creep by either thickening the backspans or staple legs to prevent or reduce the deformation of the staple, or adding retaining clips or latches to preclude such deformation. Instead of trying to counteract the viscoelastic qualities of the polymer, the present invention takes advantage of these properties to provide for a dynamic response to lateral tissue forces that can deform the fastener, but not so far that the cleats of the fastener would release the tissue in the durable tissue retention zone.

Second, if tissue is being retained as opposed to skewered, large amounts of subcuticular tissue must be retained by the fastener because subcuticular tissue tends to be elastic. Grabbing smaller volumes of tissue with a fastener might not ensure that the tissue will be approximated to achieve an efficacious closure. The fastener of the present invention accommodates this requirement without the need for an excessively large or excessively strong fastener. The fastener of the present invention utilizes two different types of tissue capture zones, a first larger initial tissue capture zone that can capture a sufficient amount of tissue when the fastener is deployed to counteract the initial elasticity of the tissue and still obtain an efficacious fastening. A second set of much smaller durable tissue retention zones within the cleats are then used to provide long term holding force while the main body of the fastener can dynamically reform in response to the lateral forces exerted by the tissue during the healing process.

Finally, when fastening opposing sides of a wound, the opposing sides must be physically approximated during placement of the fastener. Once the opposing sides have been retainably fastened, the opposing sides tend to return to a more relaxed disposition during the healing process, thereby increasing lateral pressure on the bioabsorbable fastener. In conventional practice, the bioabsorbable fastener ends up being over-designed in order to assist in the initial approximation of the tissue that can result in a design that is more susceptible to failure as a result of the longer term lateral pressures applied during the wound healing process. In contrast, the bioabsorbable fastener of the present invention is designed for use with an insertion apparatus that mechanically approximates the opposing sides of wound tissue to insure the creation of consistent and repeatable pierced openings into which the fastener is positioned in a through-and-through manner to take advantage of elastically securing the tissue within the durable issue retention zones created by the cleats of the fastener.

DETAILED DESCRIPTION OF THE PREFERRED EMBODIMENTS

Figure 1:
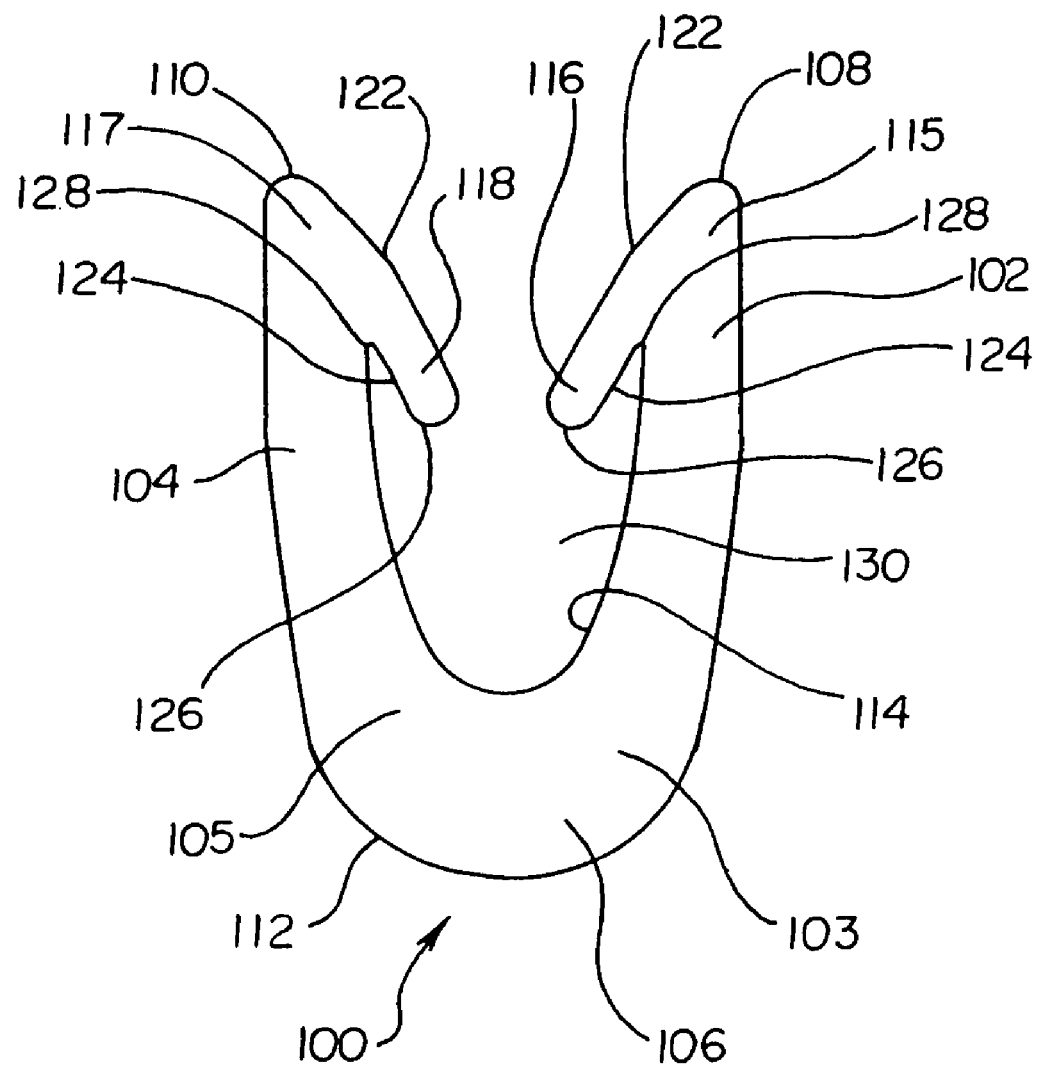
FIG. 1 is a top view of a fastener of the present invention.
Figure 2:
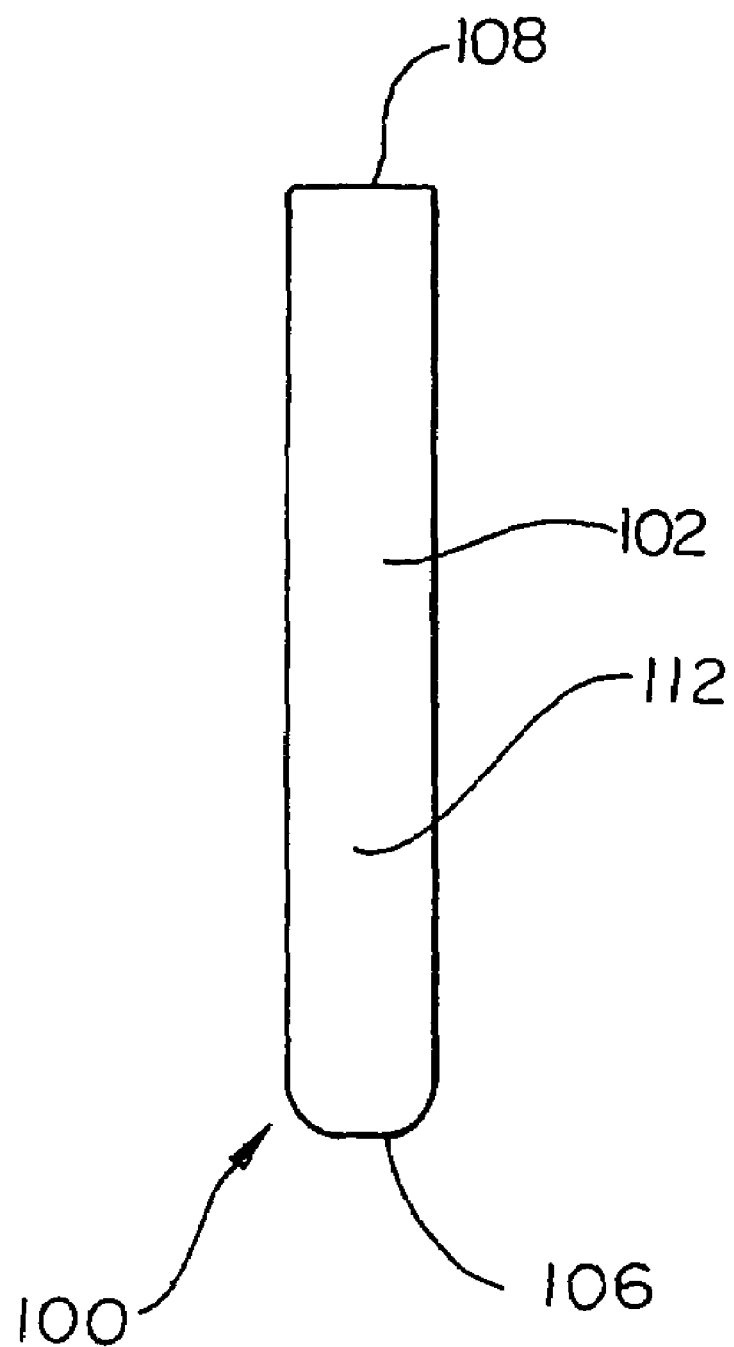
FIG. 2 is a side view of the fastener of FIG. 1.
Figure 3:
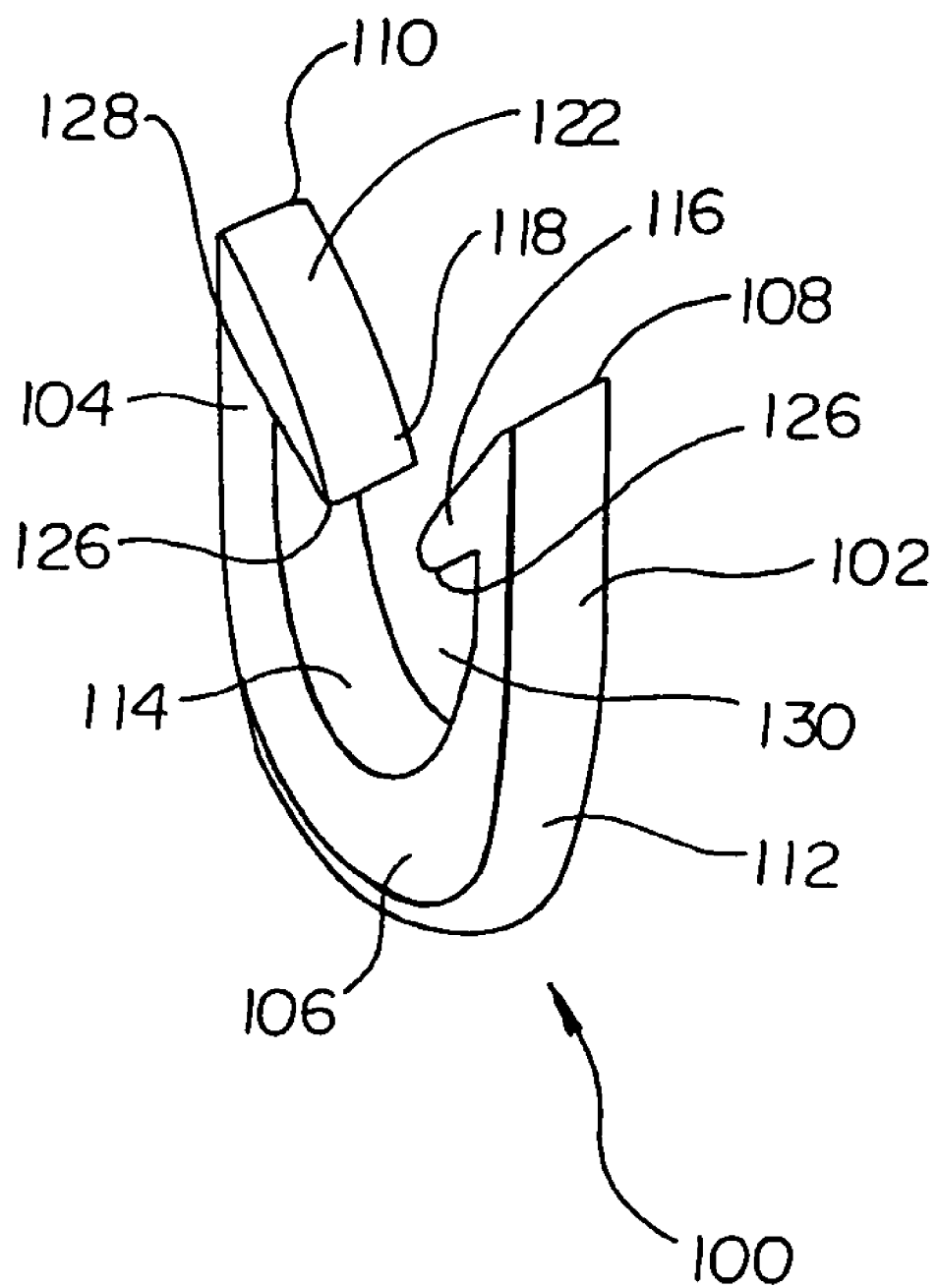
FIG. 3 is a perspective view of the fastener of FIG. 1.

Depicted in FIGS. 1–3 is a preferred embodiment of a dynamic, bioabsorbable fastener 100 of the present invention. Generally, fastener 100 comprises a pair of arms 102, 104 being operably connected with a common backspan 106 at shoulder portions 103 and 105, also depicted in FIG. 5, respectively. Arms 102, 104 each preferably include a rounded tip 108, 110. Fastener 100 is further defined by an arcuate exterior, perimeter surface 112 and an arcuate interior surface 114. The arcuate shape of interior surface 114 functions to even out and focus staple loading forces and reduces potential rocking of fastener 100 when in place within tissue. Most typically, fastener 100 has a generally circular cross-section taken through backspan 106 that gradually tapers to a more rectangular cross-section. In order to facilitate mold removal, fastener 100 can include a plurality of distinct segments and surfaces as shown for example in FIGS. 3 and 29.

Figure 4:
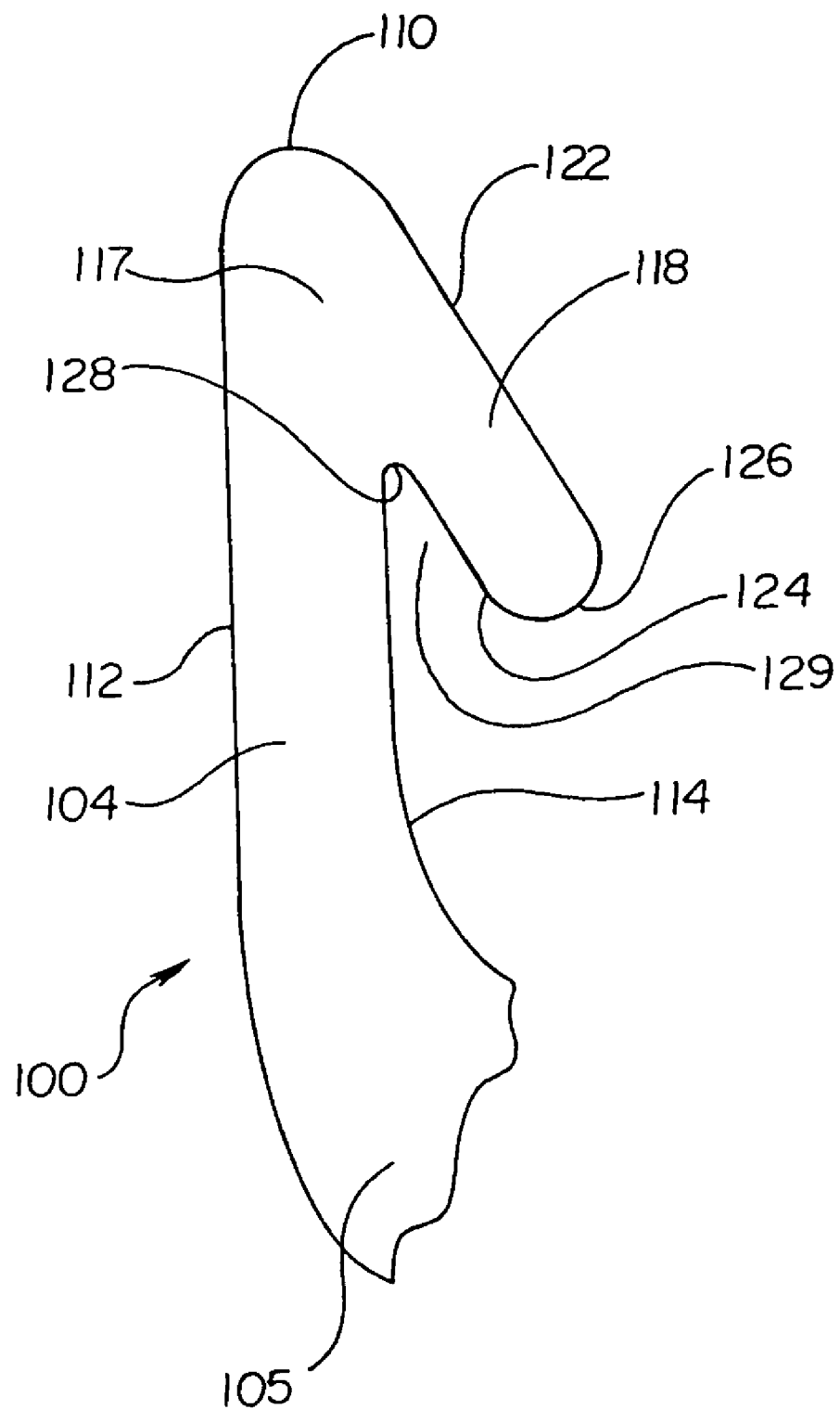
FIG. 4 is a top view of a fastener arm of the fastener of FIG. 1.

Depending from each of tips 108, 110 at an elbow region 115, 117 is a rounded cleat 116, 118. As is more clearly depicted in FIG. 4, cleats 116, 118 are defined by an outwardly facing cleat surface 122, an inwardly facing cleat surface 124 and a rounded cleat tip 126. Inwardly facing cleat surface 124 connects to interior surface 114 at a cleat base 128 defining a durable tissue retention zone 129. In combination, interior surface 114 along arms 102, 104 and backspan 106 along with the inwardly facing cleat surfaces 124 define an initial tissue capture zone 130.

Figure 5:
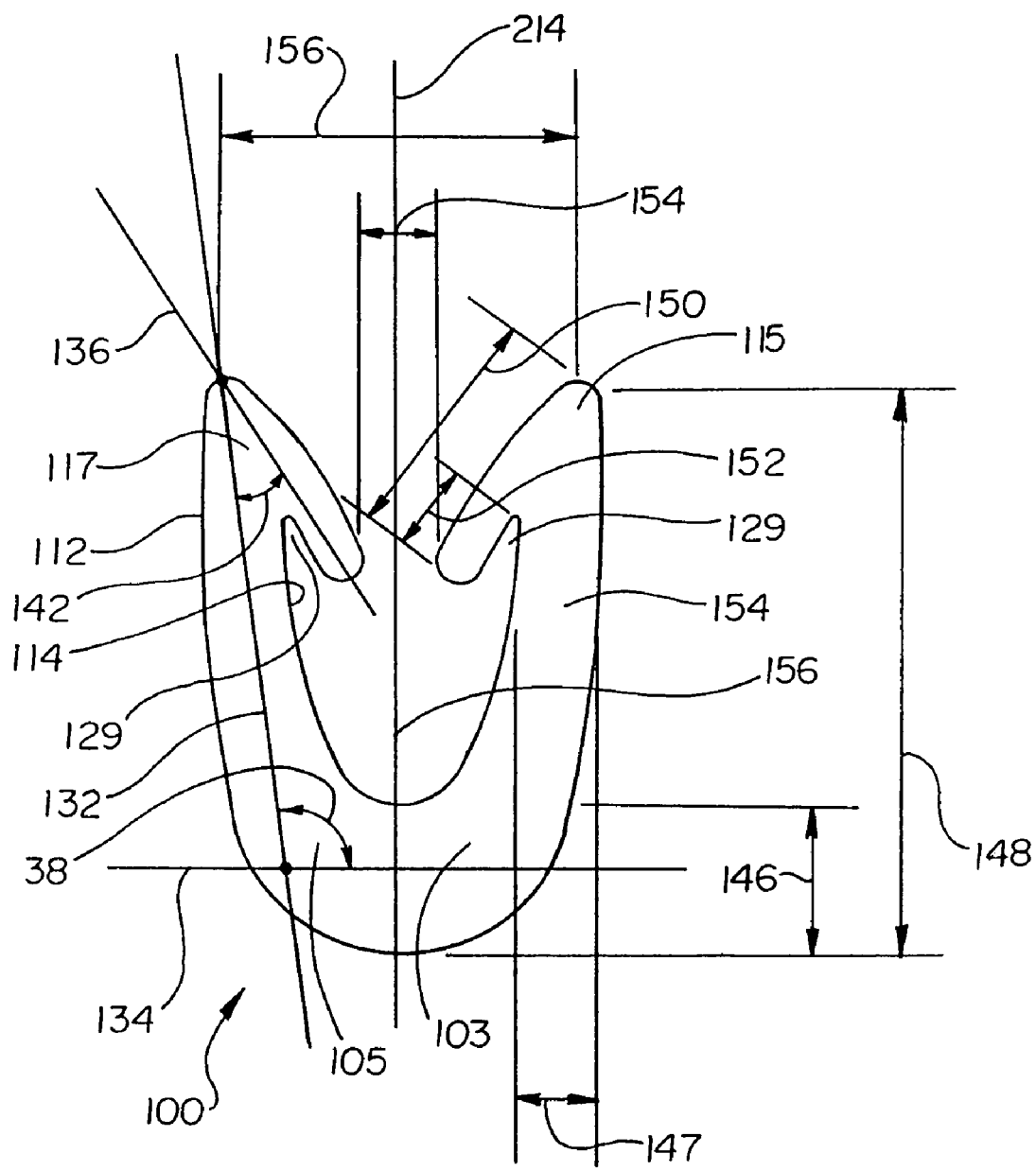
FIG. 5 is a top view of the fastener of FIG. 1.

Design elements of fastener 100 are further depicted in FIG. 5. These design elements include an effective arm center line 132, an effective backspan center line 134, and an effective cleat center line 136. With regard to effective arm center line 132, effective backspan center line 134 and effective cleat center line 136, the center lines generally refer to a line relatively equidistant between perimeter surface 112 and interior surface 114 or a line relatively equidistant between outwardly facing cleat surface 122 and inwardly facing cleat surface 124. Due to the arcuate nature of fastener 100, such center lines are only an approximation. The intersection of effective arm center line 132 and effective backspan center line 134 creates an internal shoulder angle 138 relative to fastener 100. Shoulder regions 103, 105 are defined as the areas proximate shoulder angles 138. The intersection of effective arm center line 132 and effective cleat center line 136 creates an internal elbow angle 142 relative to fastener 100. Elbow regions 115, 117 are defined as the area proximate the elbow angles 142. Other design elements include a backspan width 146, an arm width 147, an arm length 148, a cleat length 150, a cleat tip length 152, a cleat tip 126 to cleat tip 126 distance 154 and a tip-to-tip distance 156.

For purposes of a description of the present invention, fastener 100 is comprised of a generally bioabsorbable polymer selected to maintain effective retention strength for a period of at least 5 to 21 days within the body, and optimally at least 14 days before eventually being fully absorbed within the human body. Most preferably, bioabsorbable polymer comprises a blended bioabsorbable copolymer comprised of 63% polylactide and 37% polygycolide, commonly referred to as PLGA. While the PLGA copolymer is used in a preferred embodiment, other bioabsorbable polymers such as polylactide, polyglycolide and polycaprolactone, either individually, in blends or as copolymers, sharing similar traits including absorption traits, injection molding traits and polymer creep traits could be used as well. Similar to other polymers, the PLGA copolymer used in the preferred embodiment exhibits viscoelastic properties in which the entangled molecules under stress tend to slide past one another, creating a viscoelastic creep.

Due to the expense of bioresorbable polymer resins, it is preferable to avoid unncessary waste during the molding process. In order to reduce waste, fastener 100 is preferably formed using a micromolding injection molding process. Micromolding injection molding is typically used when the molding shot size is less than 1 gram. Using an appropriate micromolding injection system, for example a Battenfeld Microsystem M50, resin waste can be significantly reduced during production of a fastener 100 in accordance with the present invention. In addition, a micromolding injection system has other processing advantages such as allowing high injection speeds to promote dimensional stability, low residence times at elevated temperatures and integrated pan handling capabilities.

For purposes of maintaining wound closure during the healing process, fastener 100 is designed to supply a minimum dry initial closure strength of greater than 1.2 $lb_f$ per centimeter of wound length. In a preferred embodiment used in subcuticular wound closure, the dry initial closure strength correlates to a minimum fastener strength of 1.2 $lb_f$ per fastener 100 measured laterally between the durable tissue retention zones 129. One way to achieve a dry initial closure strength of 1.2 $lb_f$ per centimeter of wound length is to increase the amount of bioabsorbable polymer present in fastener 100 as opposed to current fastener designs. In an embodiment of fastener 100, the additional polymer is added proportionally to both the arms 102, 104 and backspan 106 to optimize the strength of fastener 100. In this embodiment, proportionally adding polymer eliminates weaknesses in fastener 100, for instance along the backspan 106, in the shoulder regions 140, in arms 102, 104 or in elbow regions 144. Such weaknesses may ultimately lead to fastener 100 failure. In this embodiment of fastener 100, the combination of the arcuate perimeter surface 112 and the arcuate interior surface 114, distribute lateral forces supplied by the tissue along the shoulder regions 103, 105. By proportionally increasing backspan width 146 and arm width 147, fastener 100 can accommodate the concentration of lateral forces without suffering a failure. Such a design optimizes the use of the expensive, bioabsorbable polymer thus eliminating unnecessary waste and expense in meeting the dry initial strength goals.

Figure 6:
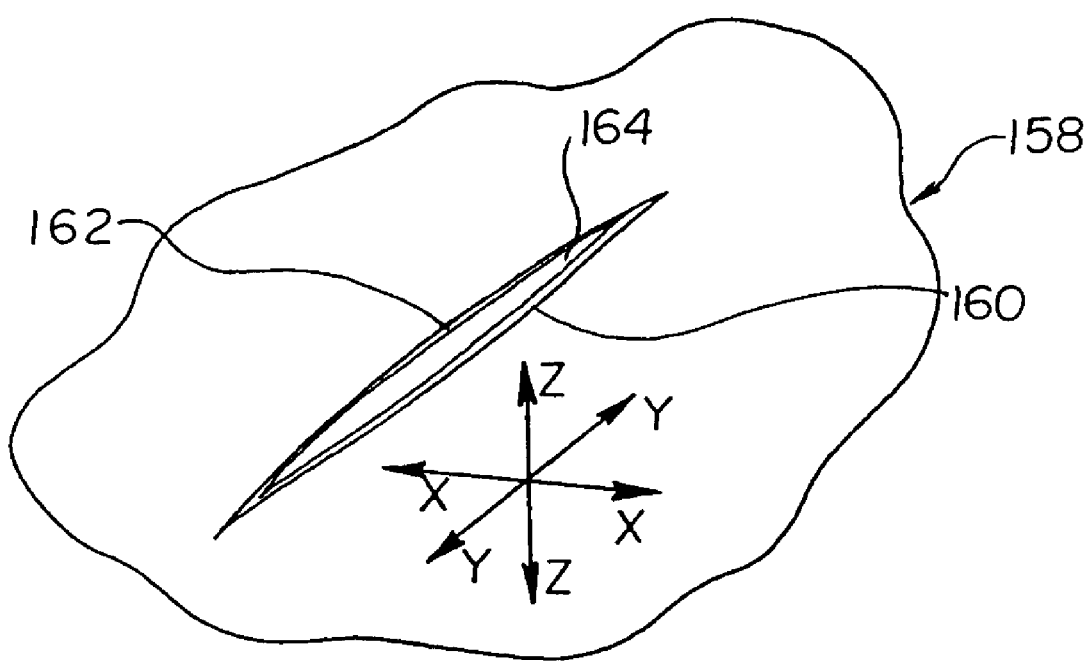
FIG. 6 is a perspective view of a skin wound.
Figure 7:
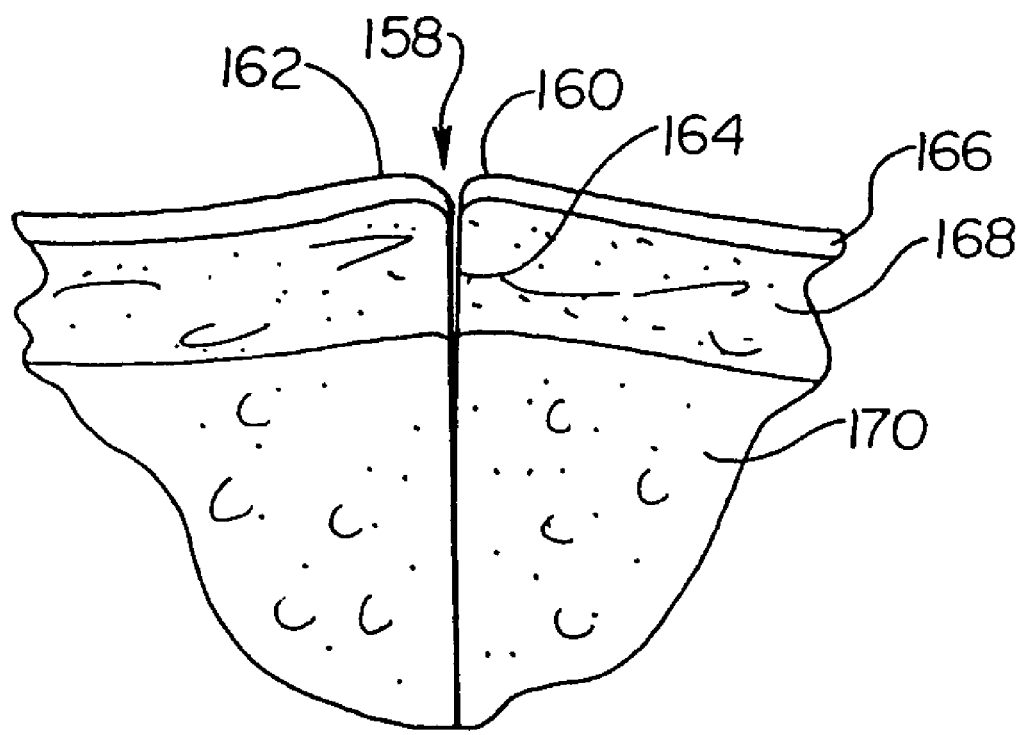
FIG. 7 is a sectional view of the skin wound of FIG. 6.

A preferred use of fastener 100 is in the subcuticular bilateral fastening of dermal tissue to close a skin wound 158, depicted in FIGS. 6 and 7, as well as in U.S. patent application Ser. No. 10/179,628 entitled., "Mechanical Method And Apparatus For Bilateral Tissue Fastening," and U.S. patent application Ser. No. 10/448,838, which is a divisional application also entitled "Mechanical Method And Apparatus For Bilateral Tissue Fastening," both of which are commonly assigned to the assignee of the present invention and are hereby incorporates by reference in their entirety. Skin wound 158 generally comprises a pair of opposing skin surfaces 160, 162 separated by a gap 164. Gap 164 can be created through either purposeful means, such as a surgical incision, or accidental means such as an accidental cut. Opposing skin surfaces 160, 162 each comprise three distinct layers: an epidermal layer, or epidermis 166; a dermal layer, or dermis 168; and a subcuticular layer 170. The epidermis 166 comprises dead skin tissue that may hinder but does not assist in the biological healing process. The subcuticular layer 170 comprises a layer of fatty tissue typically lacking the strength necessary to anchor and hold skin closure fasteners throughout the biological healing process. Generally, a physician closes skin wound 158 by forcibly approximating the dermis 168 of opposing skin surfaces 160, 162. As the dermis 168 comprises living tissue, biological healing of skin wound 158 commences immediately upon approximation and limited healing occurs within the first 24 hours of approximation. In addition, the dermis 168 possesses enough strength and elasticity to anchor, hold and retain fastener 100.

Generally as depicted in FIGS. 8, 9, 10 and 11, a delivery device 172 incorporating a pair of piercing members 174, 176 is used to introduce fastener 100 into wound 158. Most typically, delivery device 172 includes a handle 177 and trigger assembly 178 attached to an applicator head 180 for advancing and retracting the piercing members 174, 176. Piercing members 174, 176 include a sharp tip 182 for piercing tissue as well as a semi-circular cross-section 184 defining a retaining space 186 that interfaces with and transports fastener 100 into wound 158. Cross-section 184 defines a maximum piercing width 188. Piercing members 174, 176 are connected with a backspan member 190. Applicator head 180 can also include a guide member 192, a pair of capture zones 194, 196, a pair of compression members 198, 200 and a pair of bores 202, 204.

Figure 8:
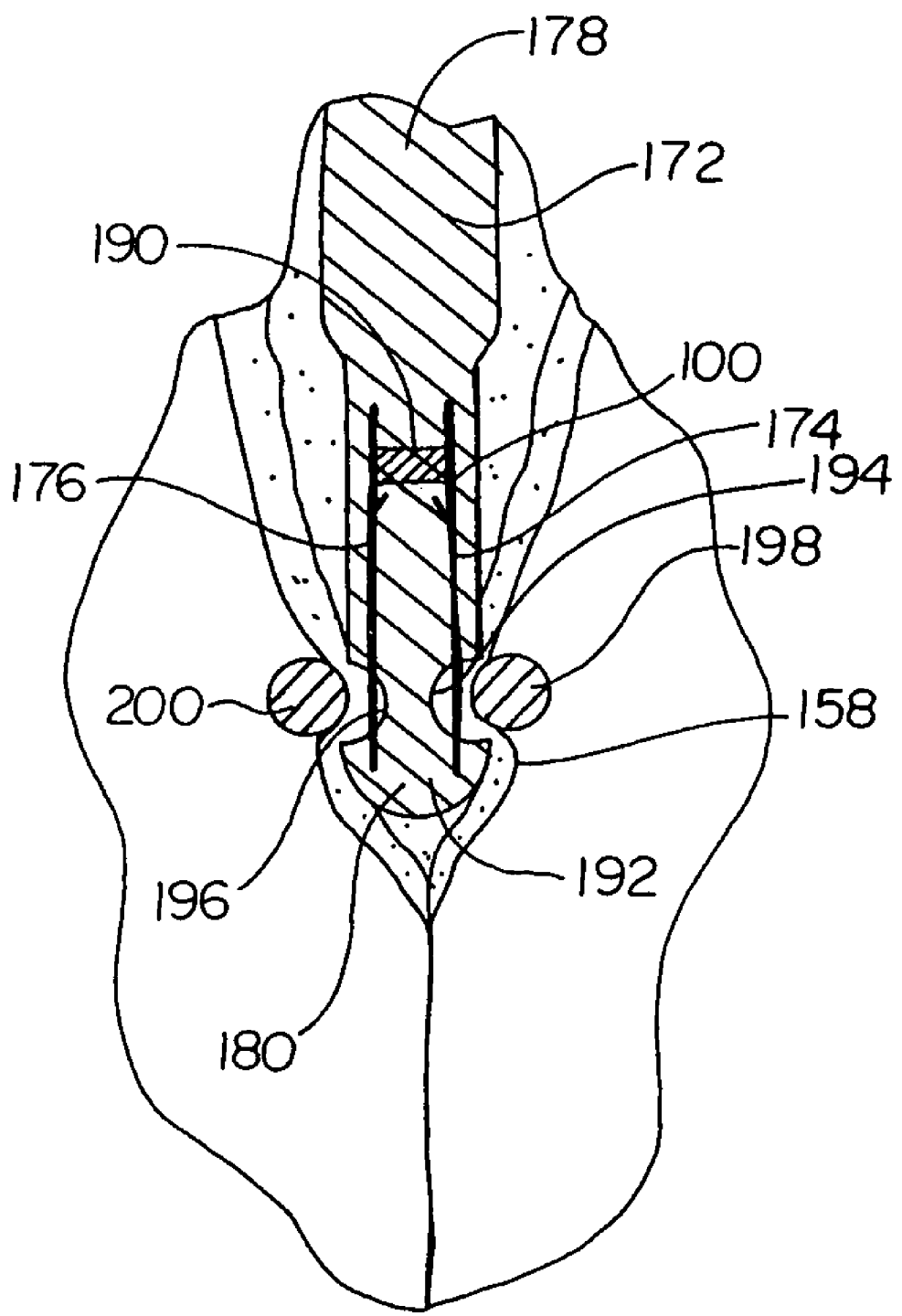
FIG. 8 is a top view of a delivery device used in closing the skin wound of FIG. 6.
Figure 9:
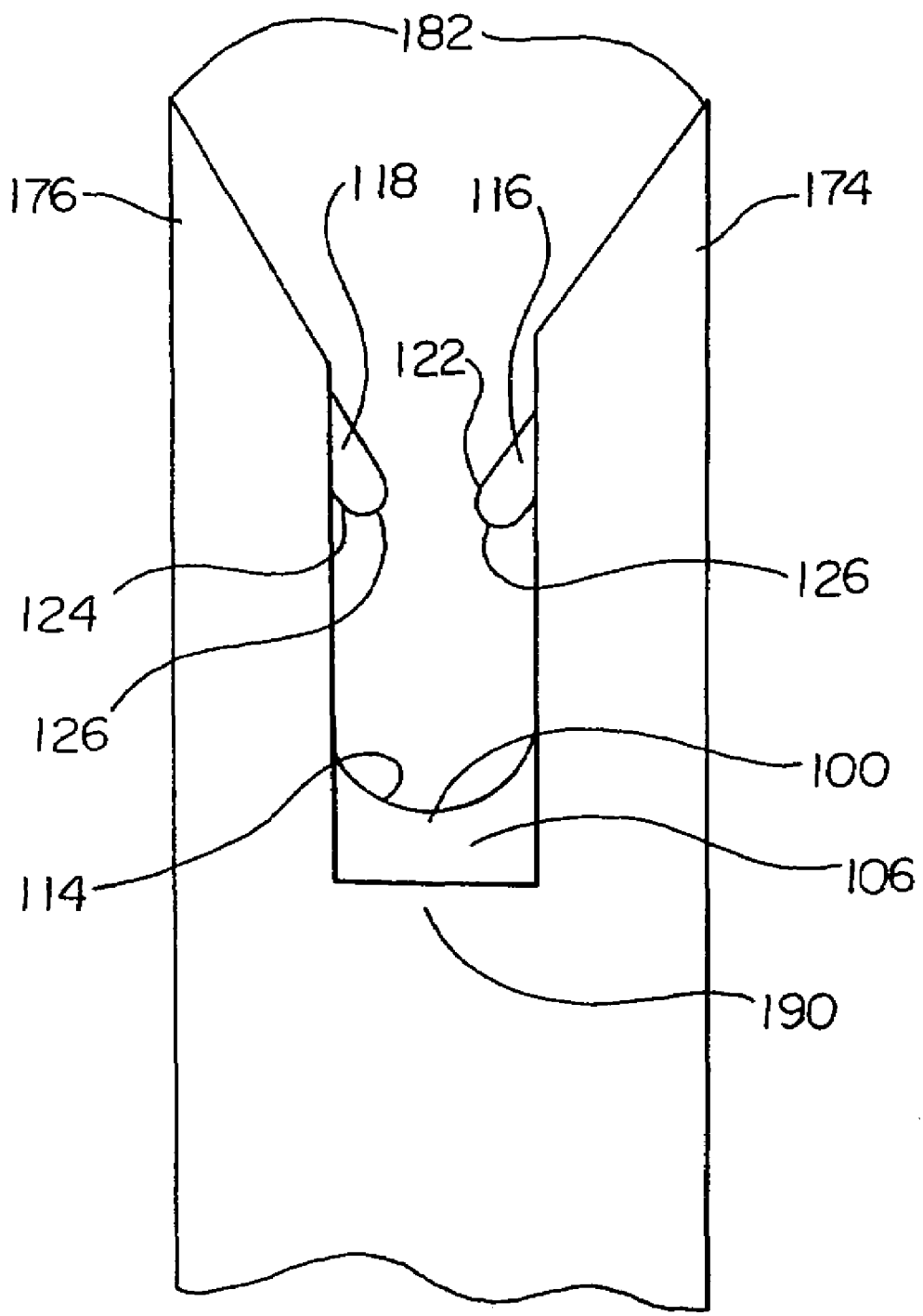
FIG. 9 is a top view of a delivery device including the fastener of FIG. 1.
Figure 10:
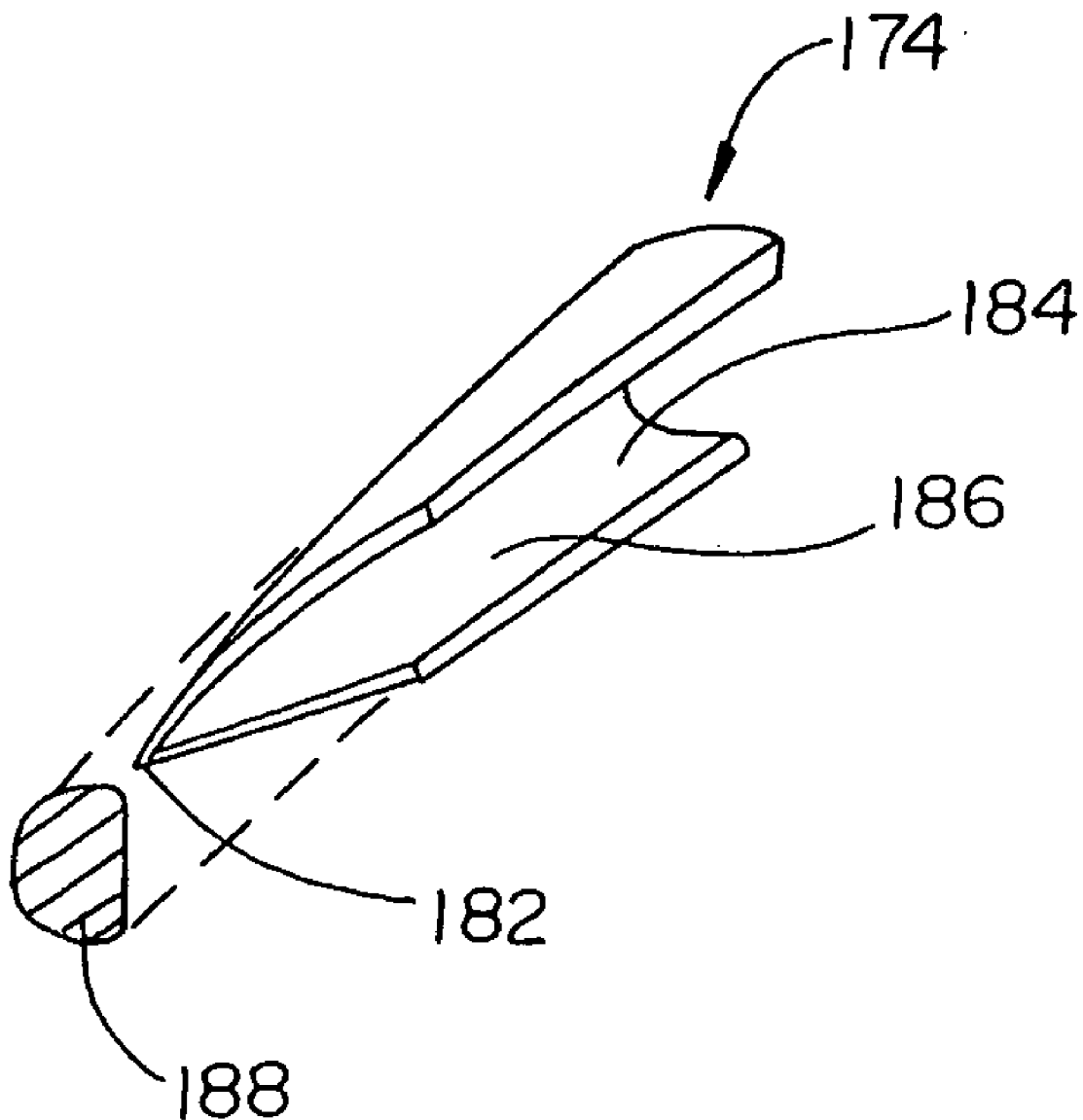
FIG. 10 is a perspective view of a piercing member.
Figure 11:
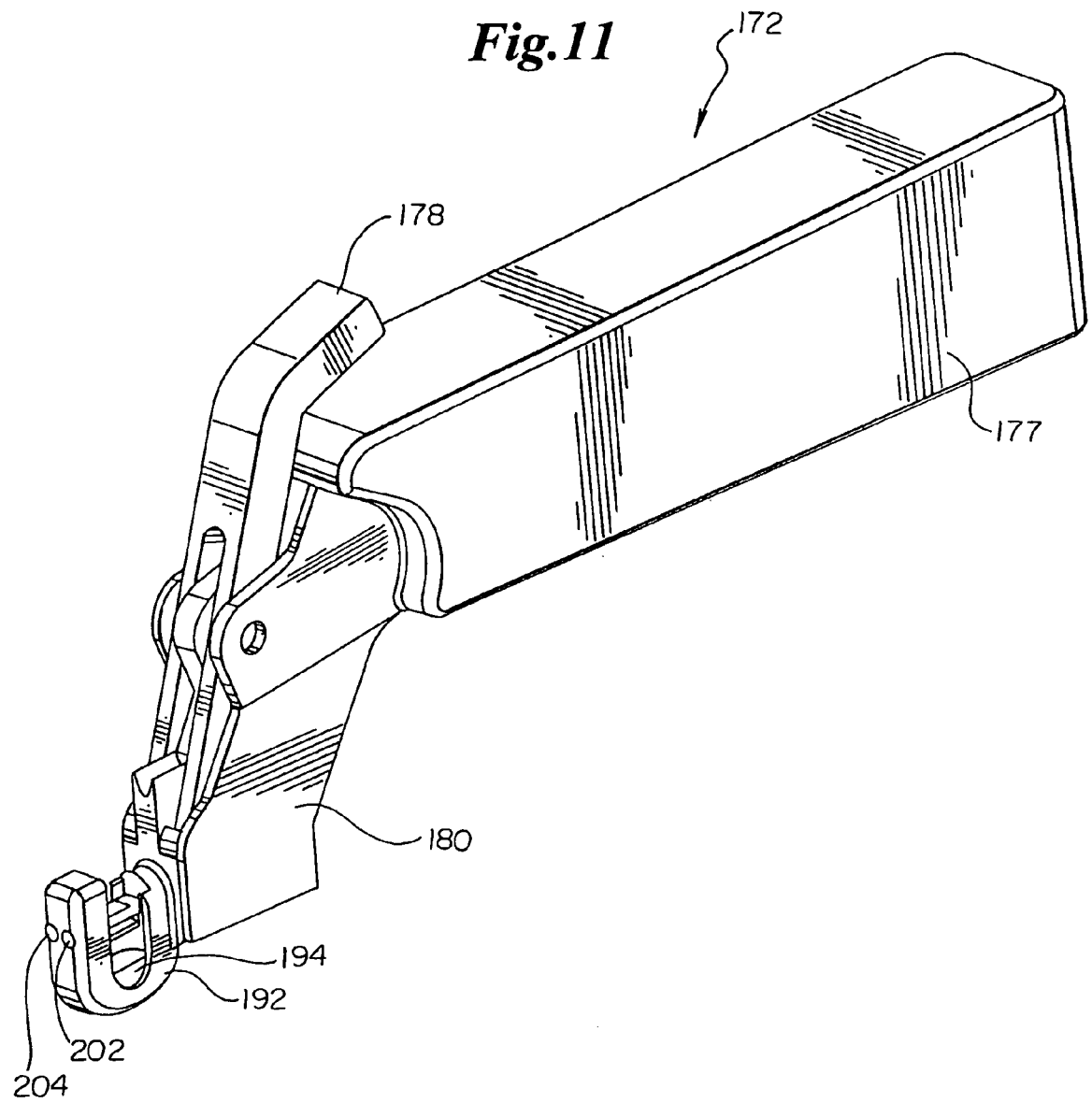
FIG. 11 is a perspective view of an embodiment of a delivery device.
Figure 12:
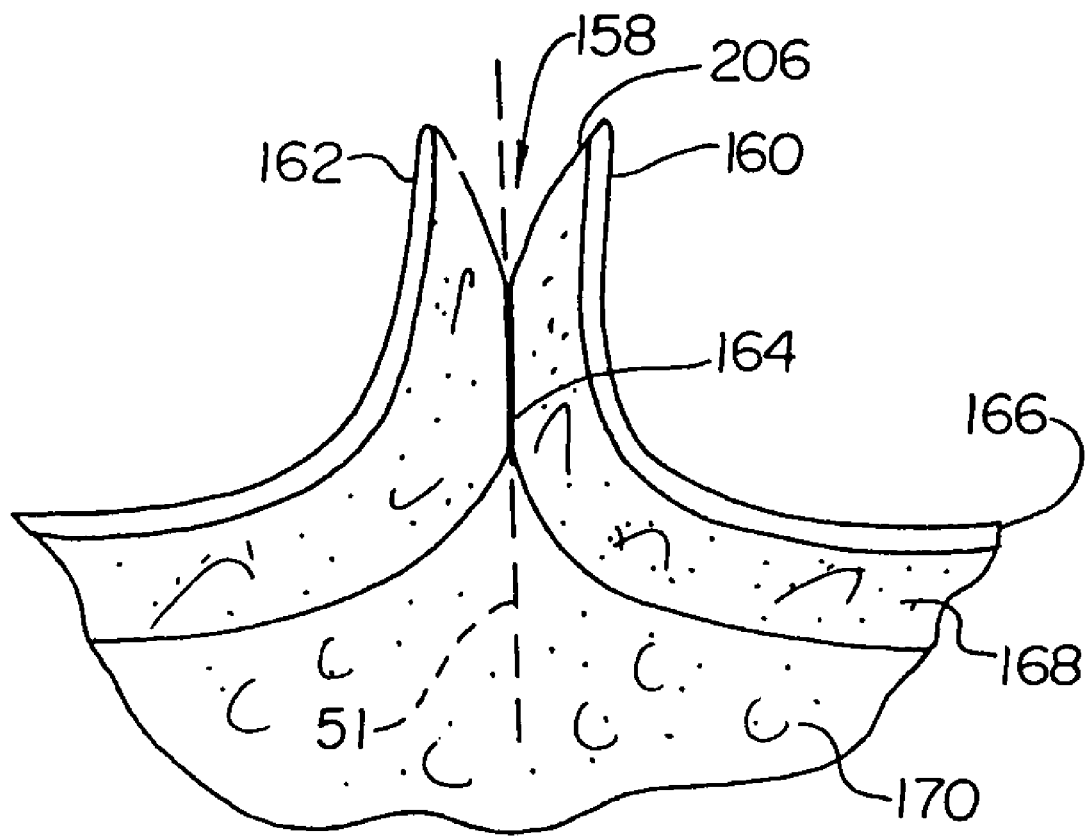
FIG. 12 is a sectional view of the skin wound of FIG. 6 in an everted disposition.

In a preferred use of fastener 100, subcuticular bilateral fastening of dermal tissue present in wound 158 is accomplished using a through-and-through bilateral tissue fastening technique described in the concurrently filed U.S. Patent Application entitled "Mechanical Method And Apparatus For Bilateral Tissue Fastening," which is commonly assigned to the assignee of the present invention, a copy of which is attached and the disclosure of which is hereby incorporated by reference in its entirety, In this bilateral tissue fastening technique as shown, for example, in FIG. 8, fastener 100 is loaded between piercing members 174, 176 and backspan member 190. Cross-section 184 is designed to snugly accommodate exterior surface 112 such that only cleats 116, 118 protrude inwardly from cross-section 184. Once fastener 100 has been loaded, guide member 192 is positioned within skin wound 158. Compression members 198, 200 are used to approximate opposing skin surfaces 160, 162 and force them within capture zones 194, 196. Compression members 198, 200 force skin wound 158 into an everted disposition 206 shown in FIG. 12. As will be apparent, delivery device 172 is capable of a variety of alternative embodiments including varying orientations of guide member 192, the incorporation of compression members 198, 200 into delivery device 172 and designs in which delivery device 172 includes storage and loading means allowing for a multi-shot design.

Figure 13:
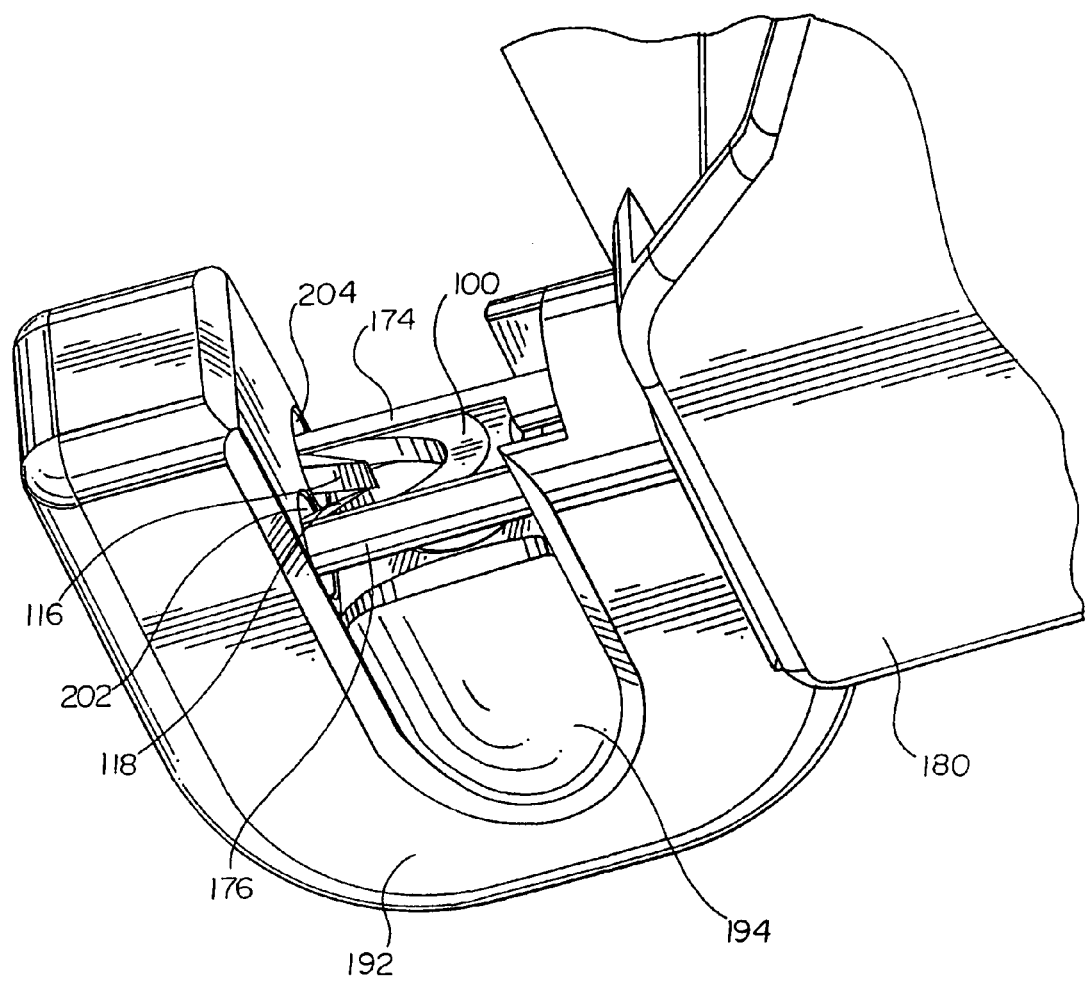
FIG. 13 is a perspective view of an applicator head including the fastener of FIG. 1.
Figure 14:
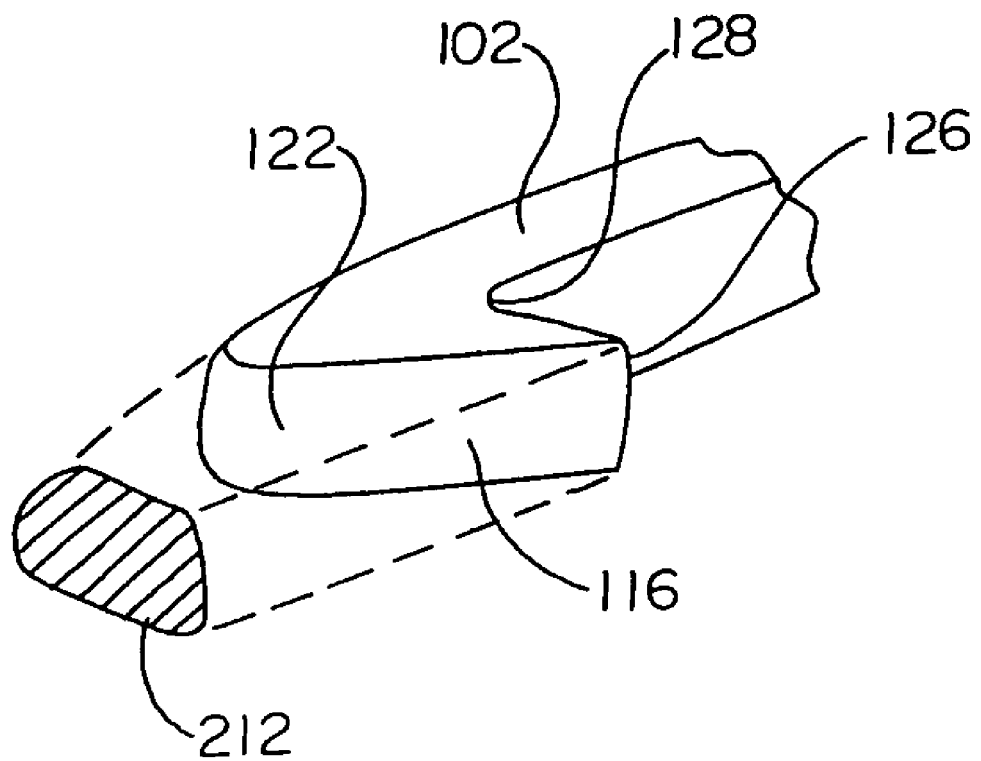
FIG. 14 is a perspective view of a fastener tip and cleat.
Figure 15:
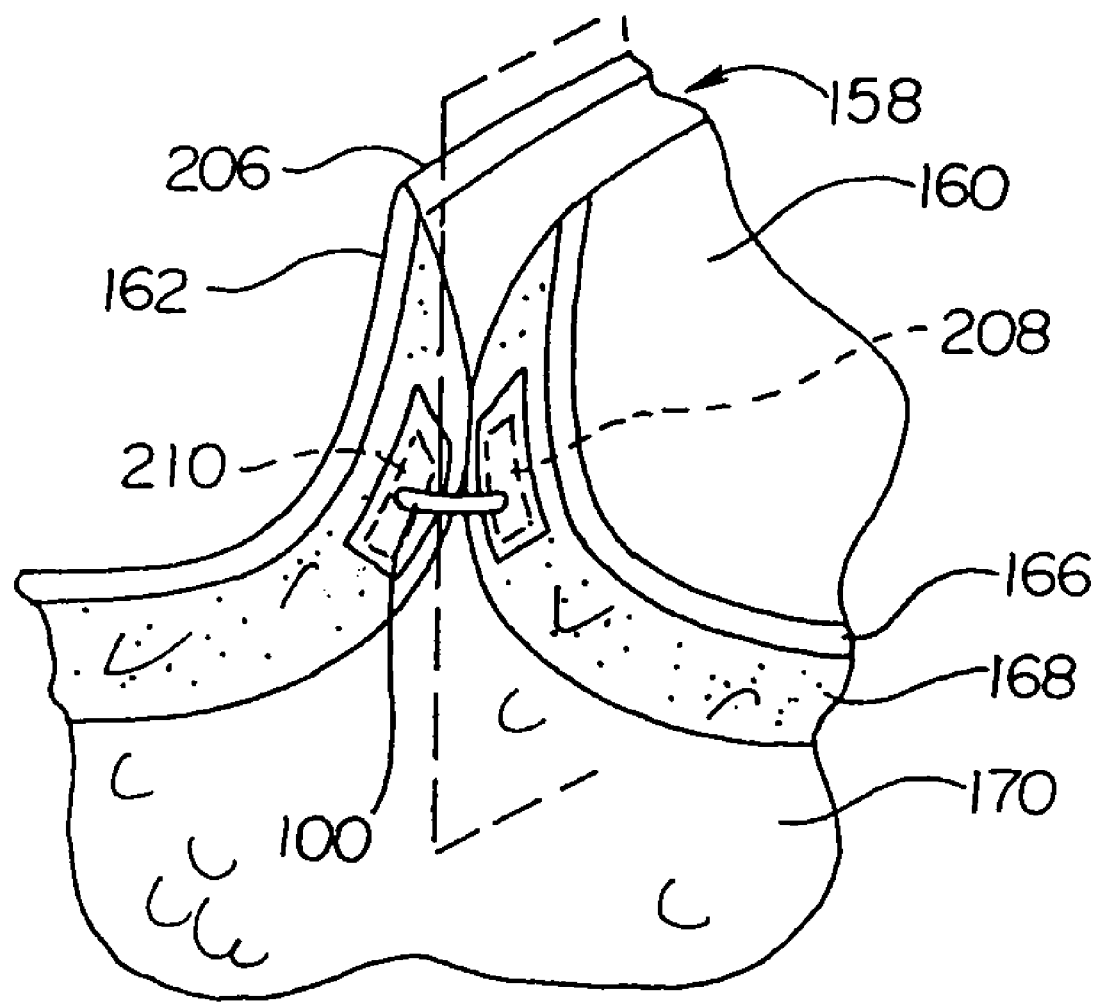
FIG. 15 is a section view of the everted skin wound of FIG. 12 including the fastener of FIG. 1 positioned within a pair of target tissue zones.

Through precise dimensioning of capture zones 194, 196, a pair of target tissue zones 208, 210 defined in the dermis 168 of opposing skin surfaces 160, 162 are presented to tips 182 of piercing members 174, 176 as depicted in FIG. 15. Using trigger assembly 178, piercing members 174, 176 are advanced forward into capture zones 194, 196 and correspondingly through the target tissue zones 208, 210 resulting in openings being pierced in dermal layer 168. Tips 182 continue to advance out of the target tissue zones 208, 210 and into the bores 202, 204 present in guide member 192 as shown in FIG. 13. As piercing members 174, 176 advance, fastener 100 is simultaneously advanced into target tissue zones 208, 210. As shown in FIG. 14, the outwardly facing cleat surface 122 of cleat 116, and similarly cleat 118, define a maximum insertion width 212 that is purposely designed and manufactured to be greater than the maximum piercing width 188 of piercing members 174, 176. Consequently, the openings pierced in the dermis 168 by tips 182 of piercing members 174, 176 must stretch to accommodate maximum insertion width 212. As cleats 116, 118 are advanced into bores 202, 204, dermis 168 is forced to elastically stretch past the tips 126 of cleats 116, 118. Dermis 168 then rebounds and elastically snaps into position around cleat bases 128 and into durable tissue retention zone 129.

Figure 16:
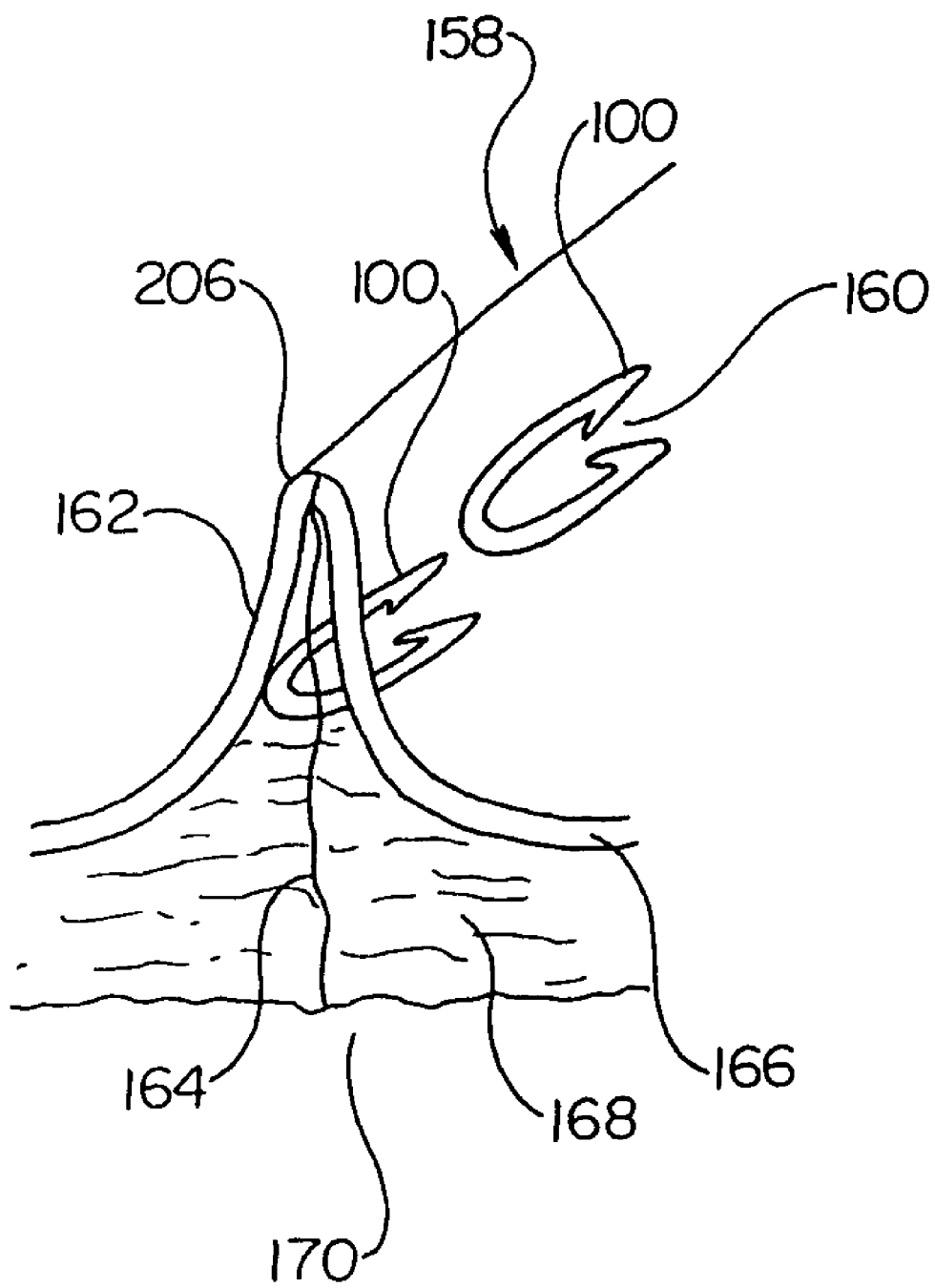
FIG. 16 is a section of the everted skin wound of FIG. 12 including a plurality of the fasteners of FIG. 1.

Using trigger assembly 178, piercing members 174, 176 are sequentially withdrawn from bores 202, 204, target tissue zones 208, 210 and capture zones 194, 196. However, fastener 100 remains within target tissue zones 208, 210 as cleats 116, 118, durable tissue retention zone 129 and especially cleat bases 128 cooperate to retain the captured dermis 168, preventing fastener 100 from being withdrawn. Backspan 106 traverses gap 164, such that opposing skin surfaces 160, 162, and especially dermis 168, are forcibly approximated to promote the biological healing process. The through-and-through insertion method is typically repeated along the length of skin wound 158 such that a plurality of fasteners 100 cooperate to forcibly close skin wound 158 as depicted in FIG. 16. Through the use of multiple fasteners 100, the minimum dry initial closure strength can be increased beyond the typical 1.2 $lb_f$ per centimeter of wound length by reducing the distance between fasteners 100 along skin wound 158. Correspondingly, the use of multiple fasteners 100 allows fastener 100 to be sized and designed for other wound closure applications or on differing locations of the body. In the preferred embodiment, fastener 100 is placed within skin wound 158 such that it resides generally parallel to the skin surface.

Figure 17:
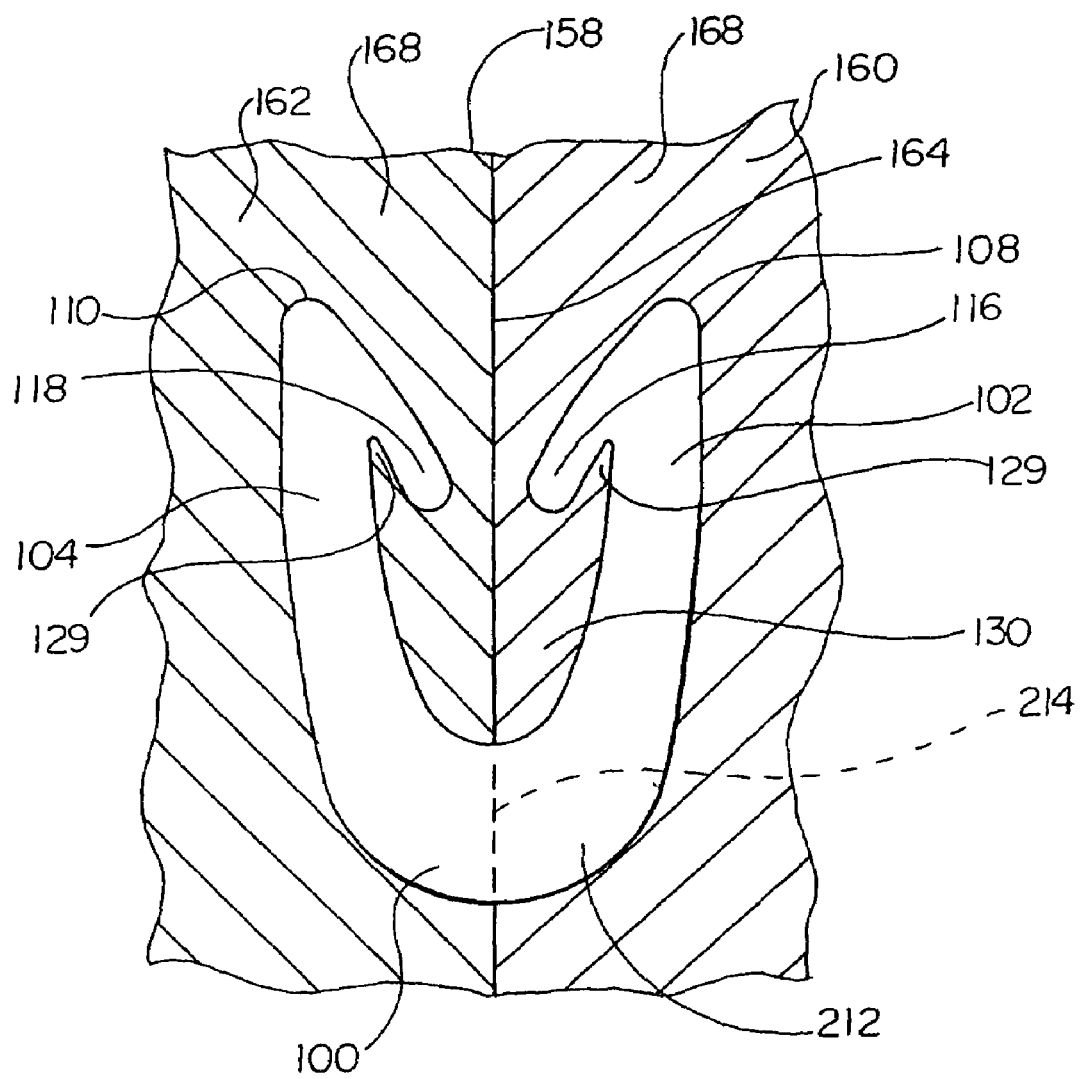
FIG. 17 is a top view of the fastener of FIG. 1 positioned within the skin wound of FIG. 6.
Figure 18:
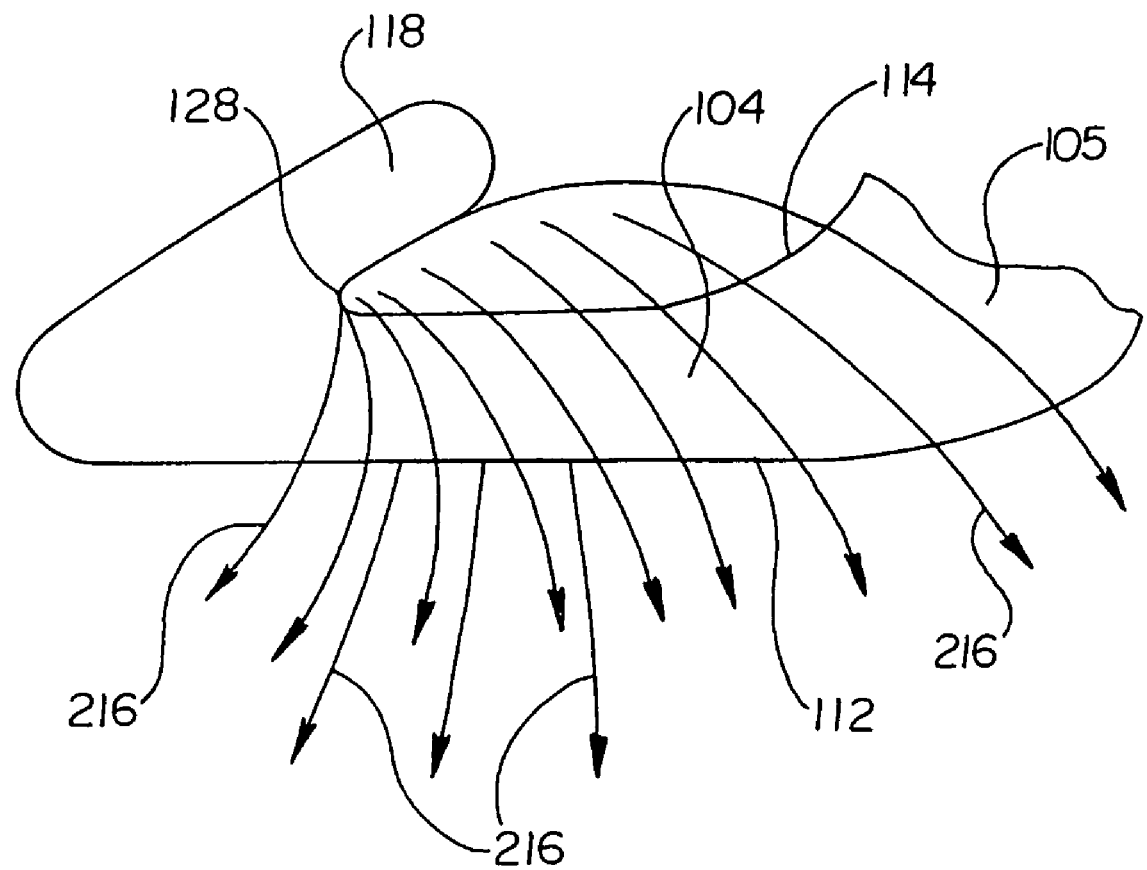
FIG. 18 is a top view of lateral forces presented along a fastener arm and cleat.

As depicted in FIG. 17, fastener 100 is shown following insertion into wound 158 via the through and through method. Prior to and immediately following wound closure, fastener 100 is present in a first disposition 212 having initial tissue capture zone 130. When in first disposition 212, shoulder angle 138 is slightly greater than 90°, while elbow angle 142 is substantially less than 90°, most preferably about 25°. First disposition 212 is representative of fastener 100 at time of insertion, herein referred to as T1. In a preferred embodiment, fastener 100 is symmetrical around a center axis 214 depicted in FIGS. 5 and 17. However, alternative embodiments can include asymmetrical designs, for example, varying arm lengths 148, cleat lengths 150, backspan widths 146, differing shoulder angles 138 and elbow angles 142. Preferably, fastener 100 is positioned such that equal amounts of first opposing side 160 and second opposing side 162 are retained within tissue capture zone 130. Following through and through insertion of fastener 100 within wound 158, fastener 100 is exposed to a series of lateral forces 216 as shown in FIG. 18. Lateral forces 216 act along interior surface 114 from cleat base 128 to shoulder regions 103, 105 during a period of time after initial deployment of fastener 100.

To prevent fastener 100 from failing when exposed to lateral forces 216, fastener 100 is manufactured of a bioabsorbable polymer specifically selected to have polymeric creep during the healing period. If the sum of lateral forces 216 exceed the minimum dry initial closure strength of fastener 100, fastener 100 will immediately begin to reform. Once fastener 100 is placed within wound 158, the closure strength of fastener 100 begins to decrease as the combination of body temperature and body moisture begins to soften, then degrade the bioabsorbable polymer used in fastener 100. Even if the sum of lateral forces 216 do not initially exceed the maximum dry initial closure strength of fastener 100, degradation of bioabsorbable polymer will typically cause fastener 100 to reform at some time T2 subsequent to wound closure.

Figure 19:
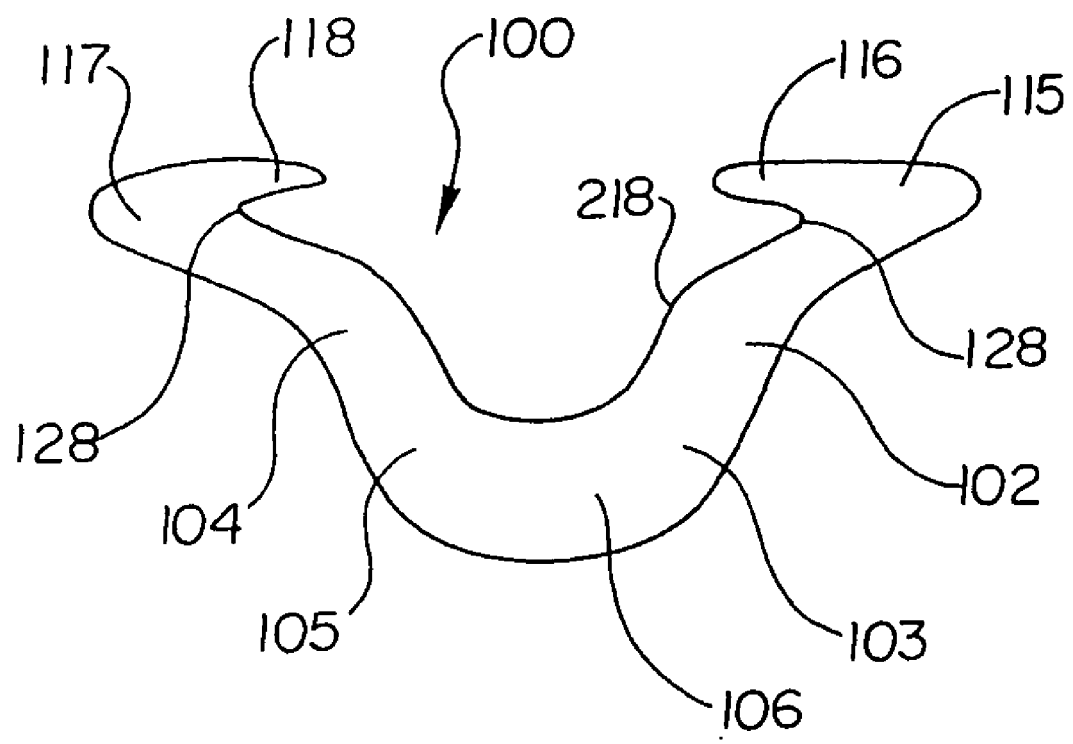
FIG. 19 is a top view of the fastener of FIG. 1 in a semi-open disposition.

Depicted in FIG. 19 is fastener 100 in a semi-open disposition 218 following exposure to lateral forces 216 greater than the fastener closure strength. Preferably, fastener 100 does not reform to semi-open disposition 218 until a period of time T2 of at least 24 hours from insertion, though depending upon placement and wound location, reformation may occur immediately upon insertion. As depicted, lateral forces 216 exceeding fastener closure strength induce polymer creep primarily in both shoulder regions 103, 105 and to a lesser degree in elbow regions 115, 117. However, fastener 100 continues to retain and approximate the captured tissue due to the continuous retention of the elastic dermis around cleat bases 128 and within durable tissue retention zones 129.

Figure 20:
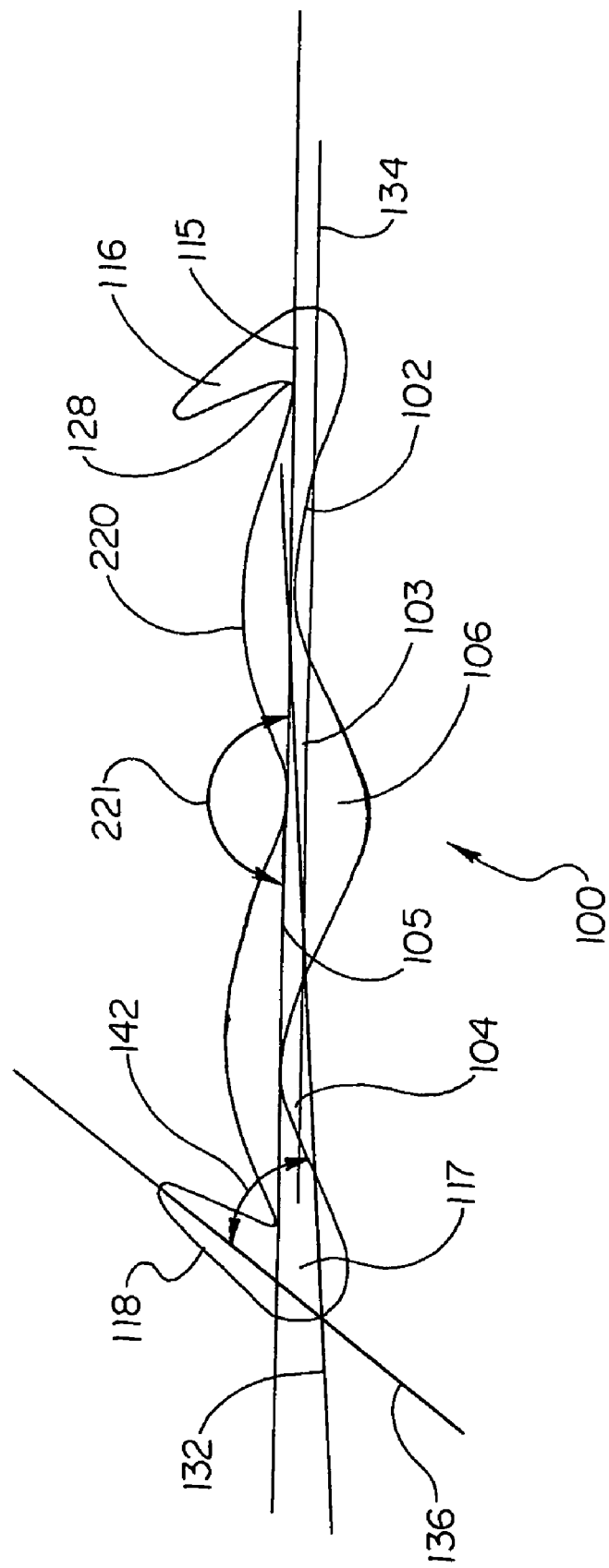
FIG. 20 is a top view of the fastener of FIG. 1 in a generally open disposition.
Figure 21:
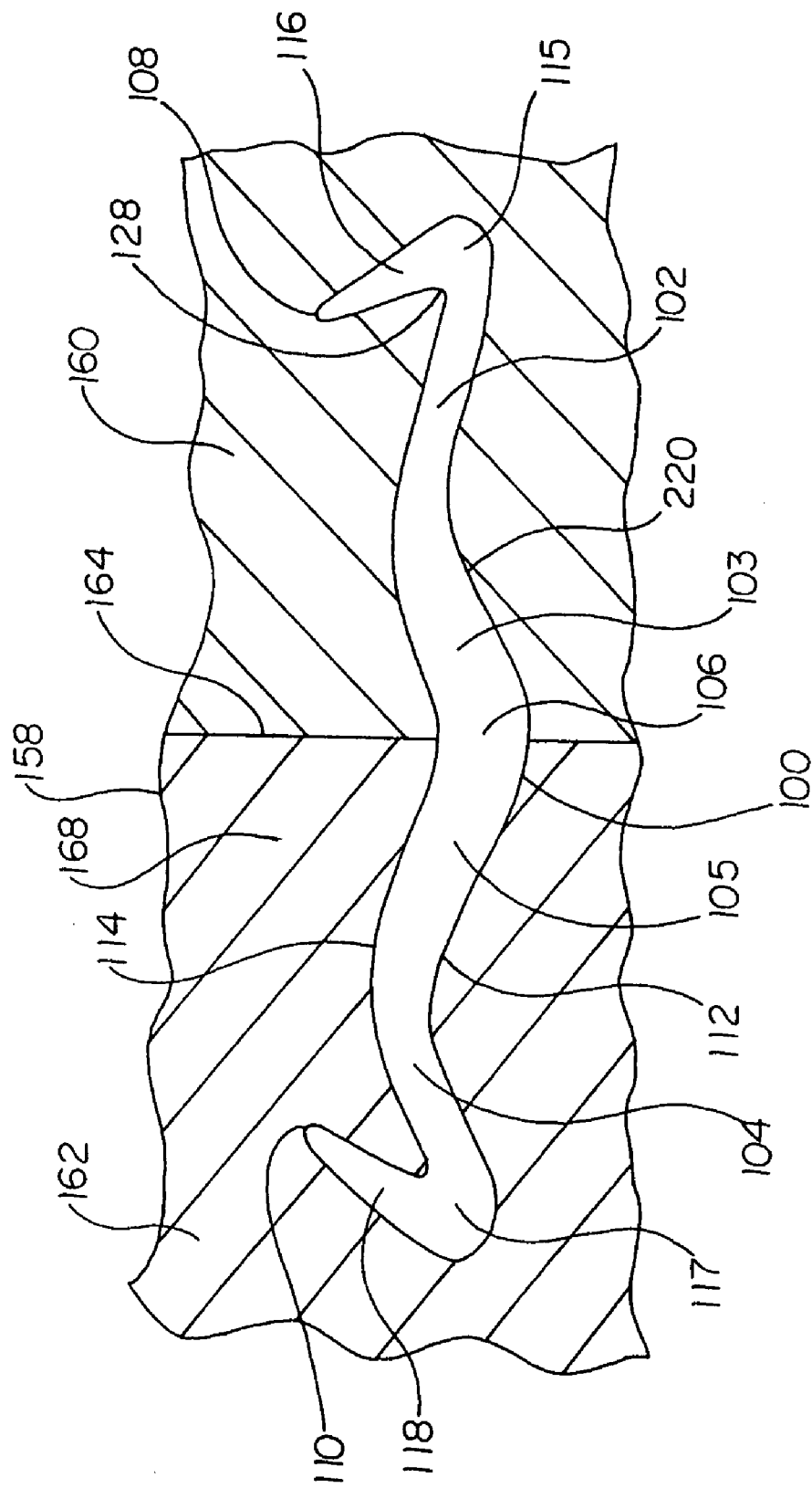
FIG. 21 is a top view of the fastener of FIG. 20 within the skin wound of FIG. 6.
Figure 22:
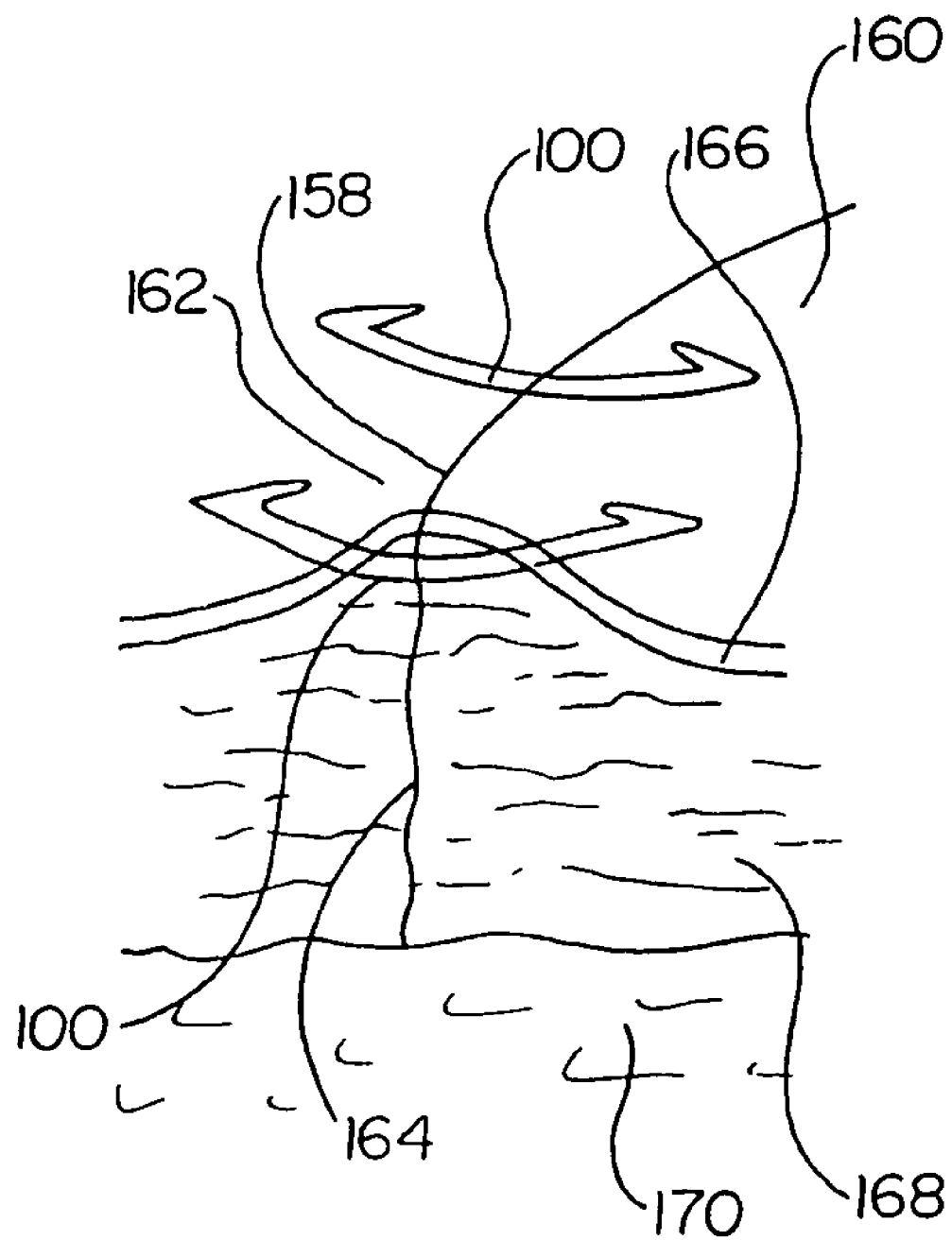
FIG. 22 is a perspective view of a plurality of the fasteners of FIG. 20 within the skin wound of FIG. 6.

Depicted in FIGS. 20 and 21, is fastener 100 in a generally open disposition 220 following exposure to lateral forces 216 exceeding those required to reform to semi-open disposition 218. Preferably, fastener 100 does not reform to generally open disposition 220 until a period of time T2 of at least 1 to 14 days and optimally at least 7 days from insertion, though depending upon placement and wound location, reformation may occur immediately upon insertion. Fastener 100 is again reformed through polymer creep in shoulder regions 103, 105 and elbow regions 115, 117. It should be noted that the closure strength of fastener 100 decreases over time due to the breakdown of the bioabsorbable polymer by the human body. As such, lateral forces 216 which may not initially be enough to induce reforming of fastener 100, will likely induce at least some degree of fastener reforming at a time subsequent to placement of fastener 100 in wound 158. In generally open disposition 220, captured tissue remains approximated during the healing process as the elastic dermis continues to be retained within cleat bases 128. In general cleat bases 128 will continue to retain the elastic dermis until the bioabsorbable polymer is absorbed to a point where failure, such as a fracture of arms 102, 104 or backspan 106 occurs or polymeric creep in elbow regions 115, 177 results in elbow angle 142 opening beyond 90° such that the elastic dermis 168 slides off of cleats 128. In generally open disposition 220, shoulder angles 138 are increasingly difficult to distinguish and instead, an internal midspan angle 221 defined by a midpoint of the backspan 106 and the apex of each durable tissue retention zone 129, is created. In the preferred embodiment of subcuticular bilateral fastening of dermal tissue as depicted in FIG. 22, a pair of fasteners 100 that have reformed to generally open disposition 220 subsequent to insertion continue to approximate wound 158. Due to the continuing capture of the dermis 168 within cleat bases 128, wound 158 remains closed throughout the healing period, typically up to twenty-one (21) days. Throughout the reformation process, the sum of elbow angles 142 and the midspan angle remains less than 360° allowing fastener 100 to continually retain captured tissue beyond the minimum degradation period. Following minimum degradation period referred to as T3, fastener 100 is increasingly likely to suffer a fracture failure of the arms 102, 104, cleats 116, 118 or backspan 106.

Figure 23:
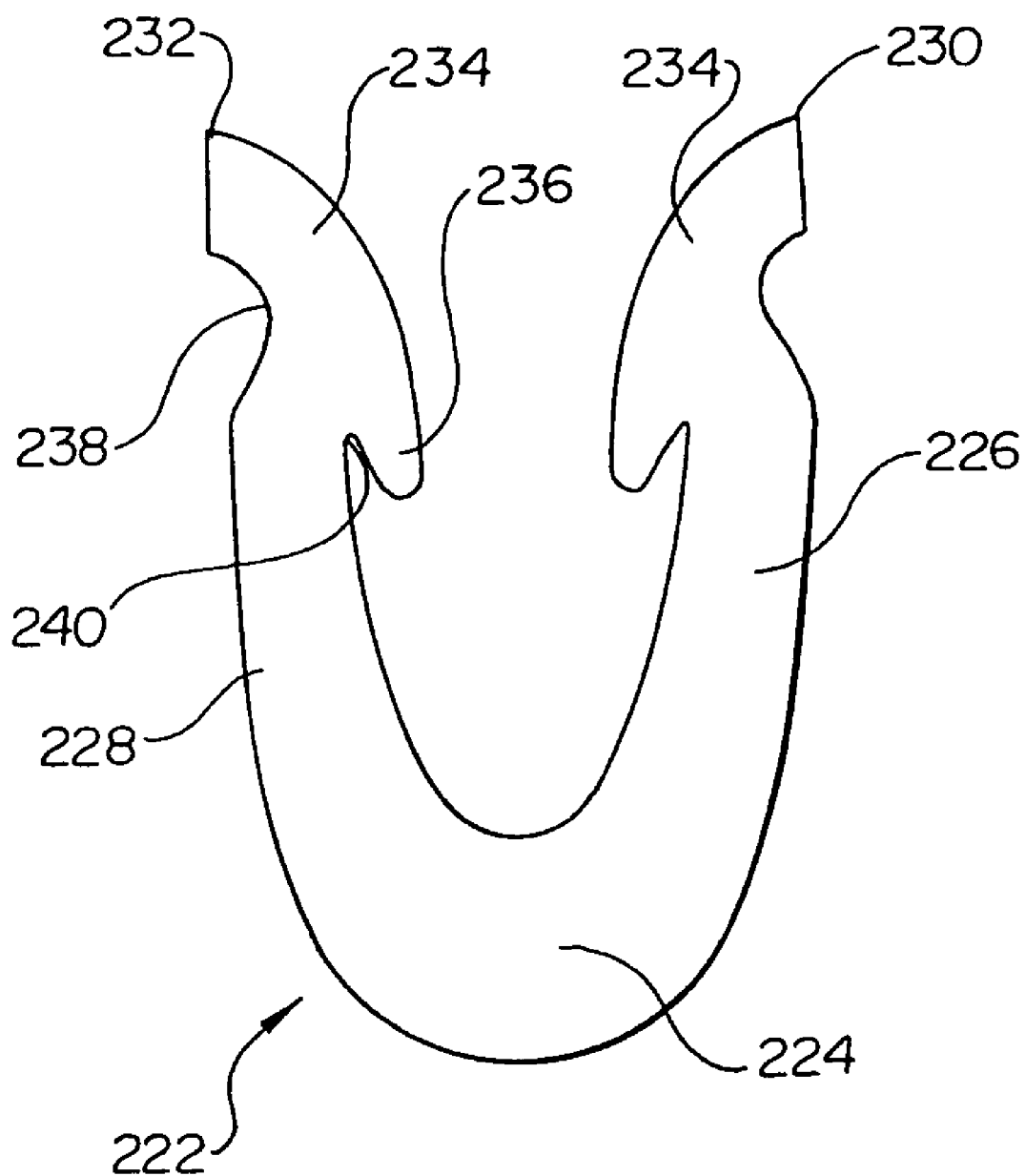
FIG. 23 is a top view of an embodiment of a fastener.
Figure 24:
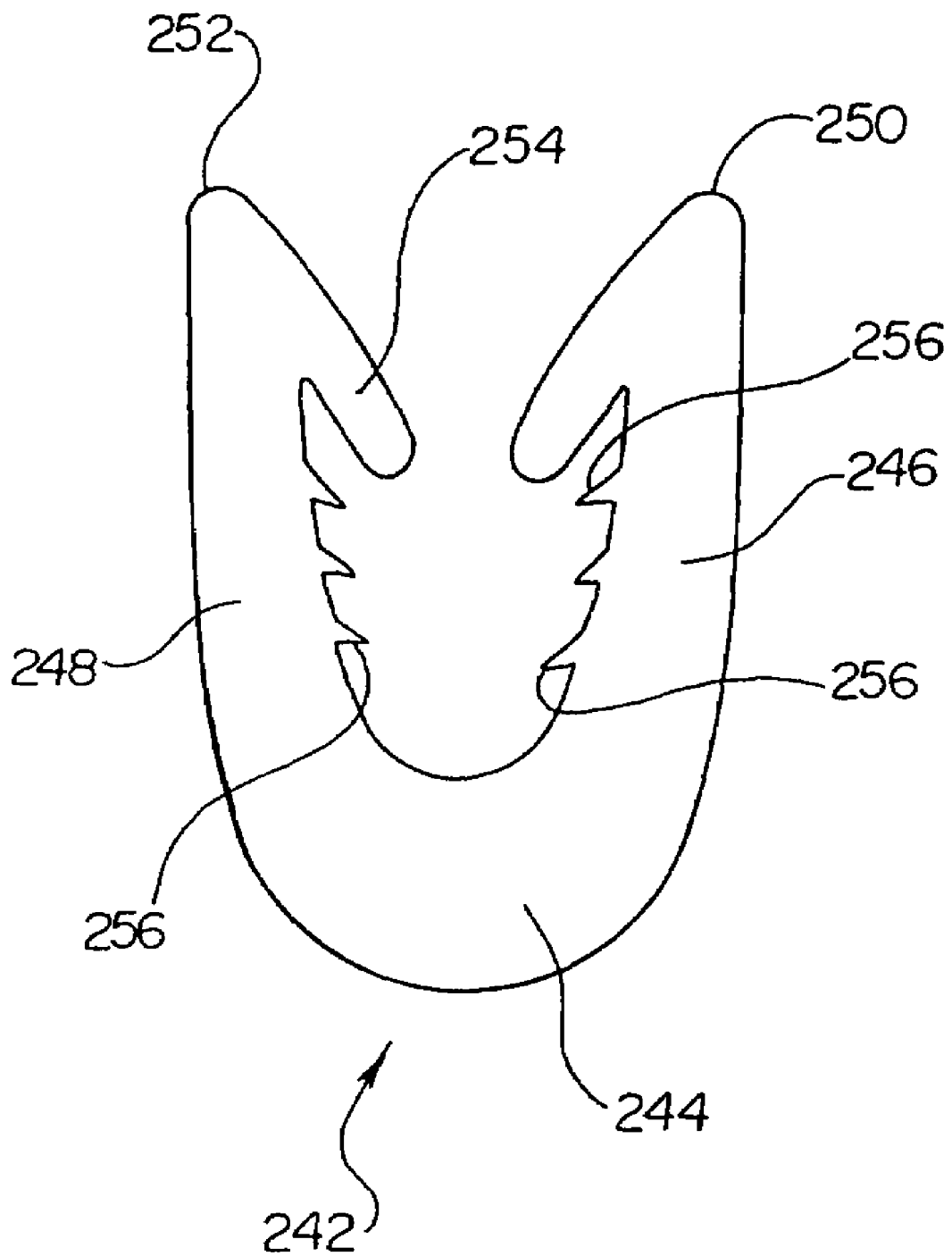
FIG. 24 is a top view of an embodiment of a fastener.
Figure 25:
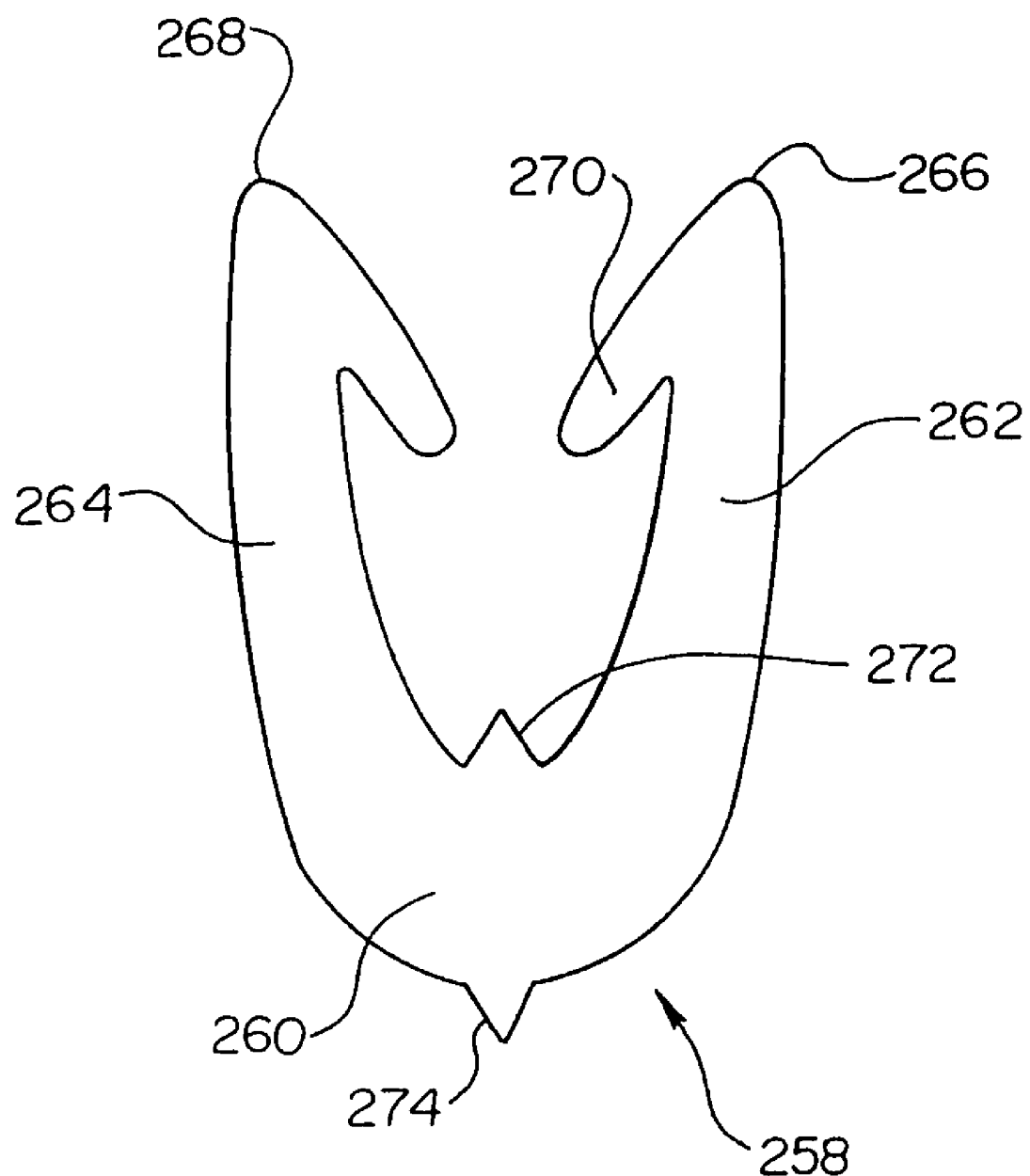
FIG. 25 is a top view of an embodiment of a fastener.

While a preferred embodiment of fastener 100 and its method of use has been described, a variety of other staple configurations featuring the same dynamic reforming traits as well as through-and-through insertion method can be utilized. For example, FIGS. 23, 24 and 25 depict alternative fastener designs incorporating additional retaining elements to further assist in wound closure. Depicted in FIG. 23, a fastener 222 comprises a backspan 224 and arms 226, 228. Arms 226, 228 include tips 230, 232 having a hammerhead orientation 234 including an internal cleat 236 and an external recess 238. Internal cleat 236 includes a cleat base 240 to similarly capture elastic tissue using the through-and-through insertion method. Depicted in FIG. 24, a fastener 242 comprises a backspan 244 and arms 246, 248. Arms 246, 248 include tips 250, 252 include an internal cleat 254 to similarly capture elastic tissue using the through-and-through method. In addition, arms 246, 248 include a series of internal projections 256 to further assist in retaining captured tissue as fastener 242 reforms in response to lateral forces supplied by captured tissue. Depicted in FIG. 25, a fastener 258 comprises a backspan 260 and arms 262, 264. Arms 262, 264 include tips 266, 268 having an internal cleat 270 to similarly capture elastic tissue using the through-and-through method. In addition, backspan 260 includes a pair of opposed projections 272, 274 to further assist in retaining captured tissue as fastener 258 reforms in response to lateral forces supplied by captured tissue. Although the fasteners of the present invention have been described with respect to an initial tissue capture zone that is defined by just two arms and within a single plane, it will be seen that a multiplicity of arms could be provided and that multiple planes could be accommodated for the tissue capture zone by, for example, making an angle in the backspan at the midpoint.

Figure 26:
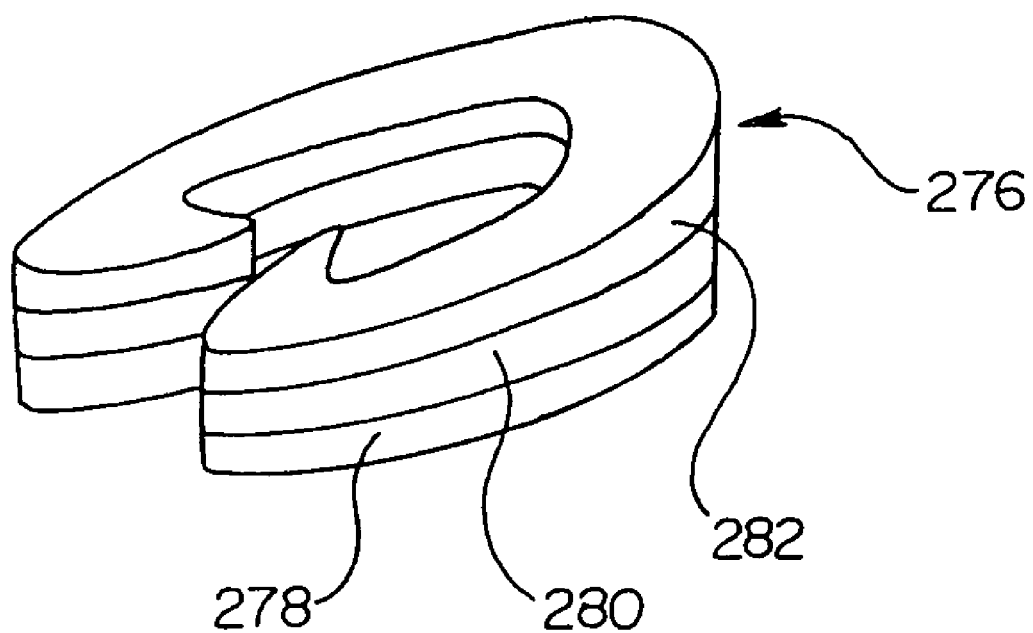
FIG. 26 is a perspective view of an embodiment of a fastener.
Figure 27:
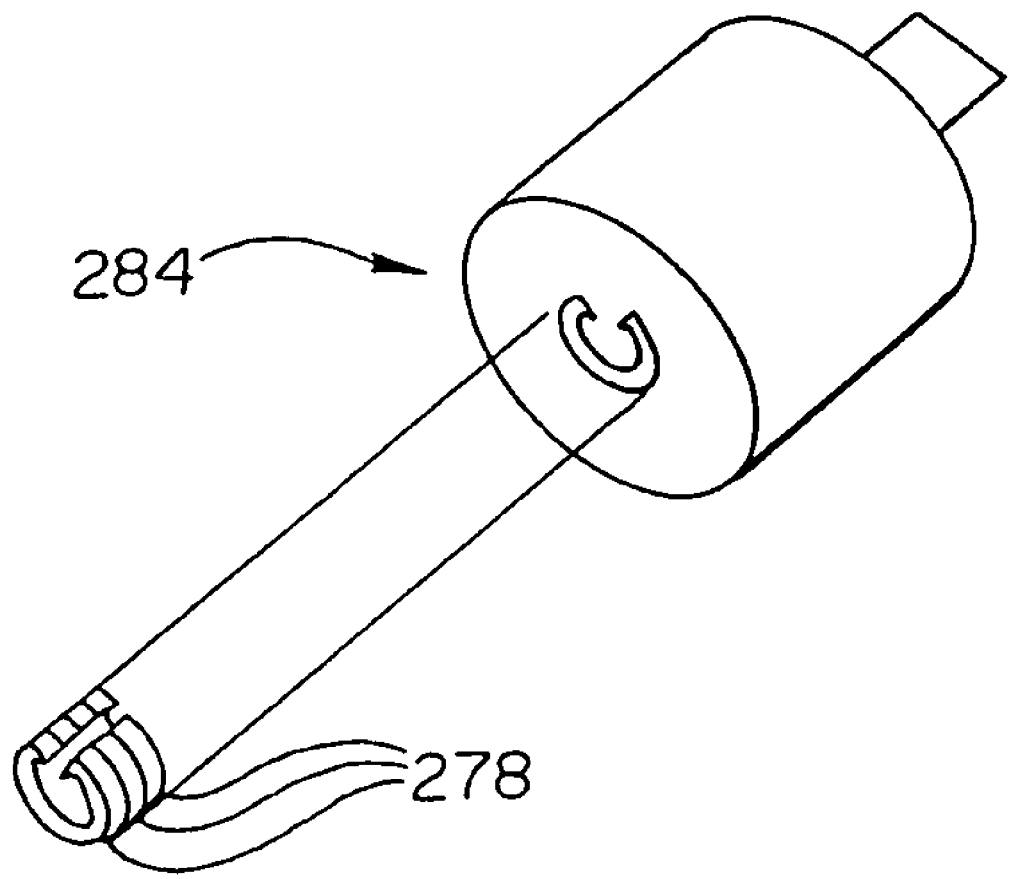
FIG. 27 is a perspective view of an embodiment of a fastener being extruded.
Figure 28:
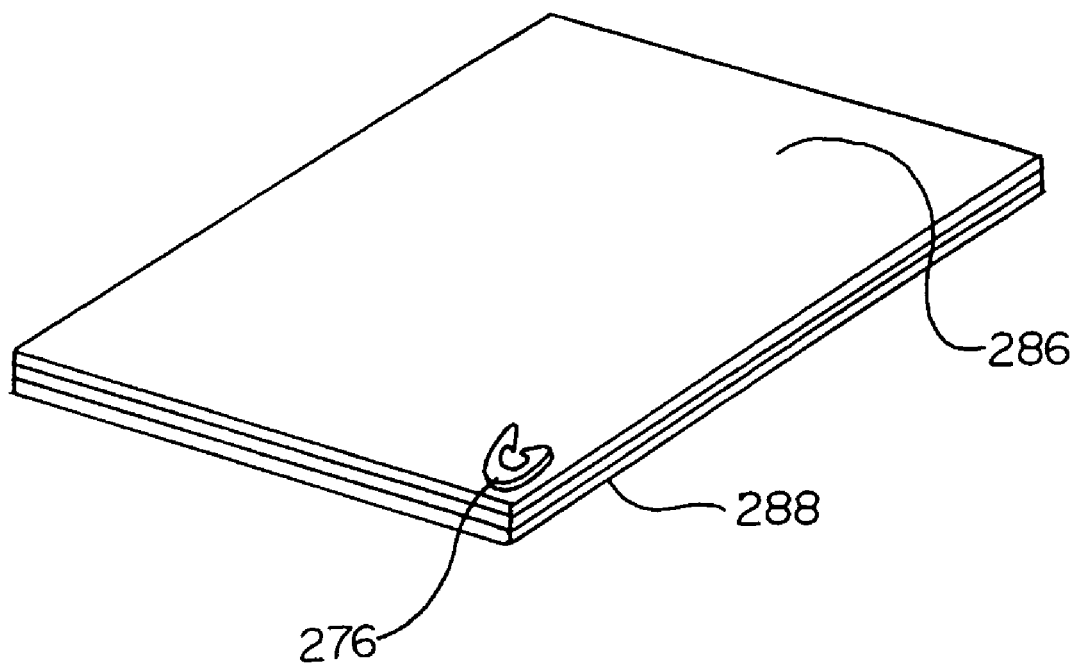
FIG. 28 is a perspective view of an embodiment of a fastener being stamped.

Depicted in FIG. 26 is another embodiment of a fastener of the present invention. A fastener 276 can comprise any of the alternative fastener configurations but in a design using at least two distinct bioabsorbable layers. As depicted, fastener 276 includes a first bioabsorbable layer 278, a second bioabsorbable layer 280 and a third bioabsorbable layer 282. While this embodiment depicts a planar arrangement of different bioabsorbable materials, it will be recognized that multiple injection points along a mold could also be used to accomplish a similar construction with different polymer materials being present at the shoulder and elbow regions, for example. In practice, fastener 276 can be formed by adhesive, thermal or molding processes where the layers are bonded after being separately manufactured using the previously described micromolding process or alternatively, through an extrusion process 284 as shown in FIG. 27. In yet another alternative manufacturing process, fastener 276 can be stamped or cut from a sheet 286 comprising a plurality of bioabsorbable layers 288 as shown in FIG. 28. Fastener 276 having multiple bioabsorbable layers 288 has a number of design advantages including the ability to mix and match faster degrading bioabsorbable polymers with slower degrading bioabsorbable polymers. In addition, fastener 276 could be used as a delivery instrument by incorporating drugs or medicants, such as antibiotics, clotting agents, or even gene therapy between layers or zones to provide a time release as the layers are broken down within the body, or even onto the exterior surfaces of the fastener to facilitate the healing process.

Figure 29:
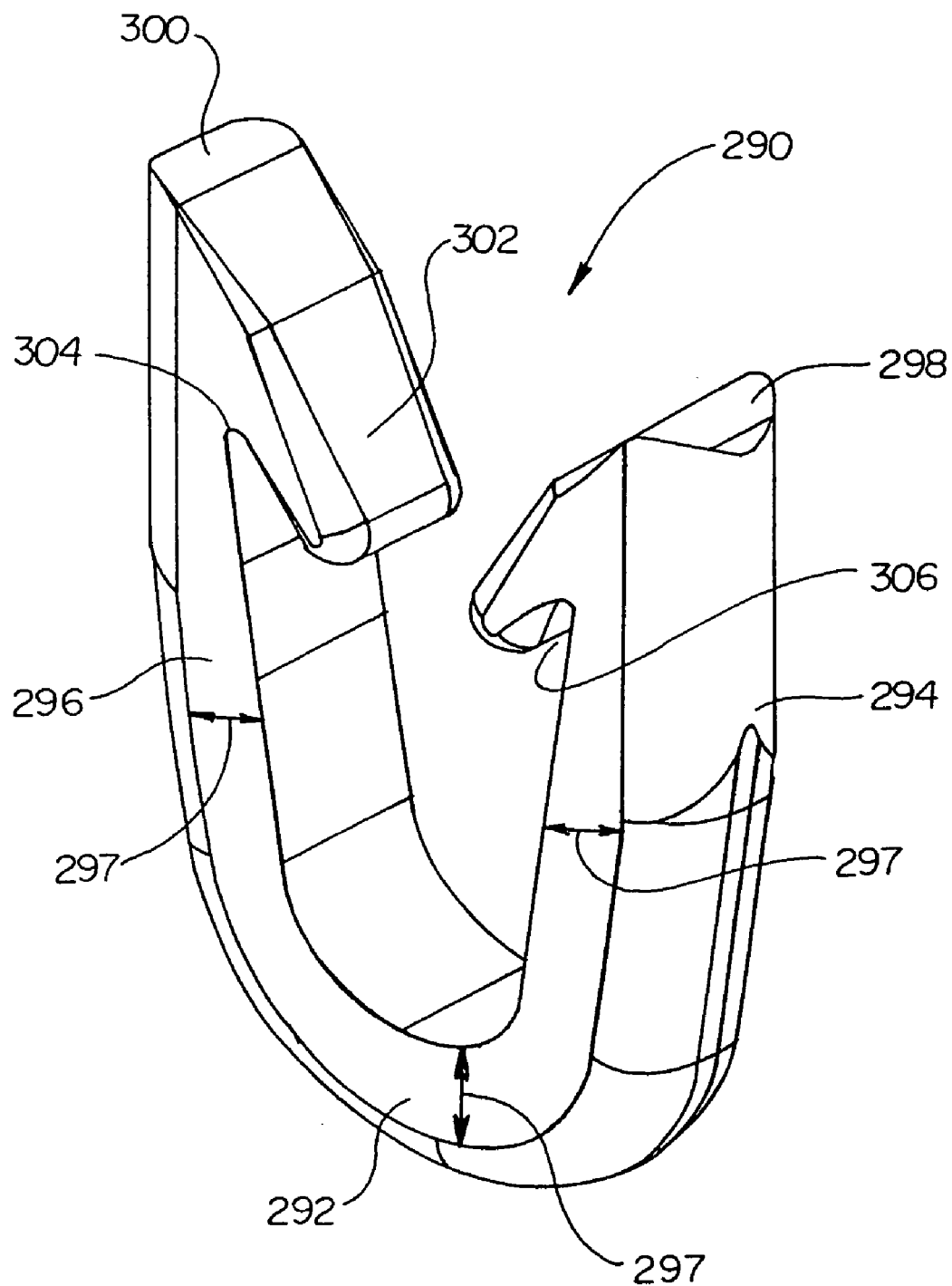
FIG. 29 is a perspective view of an embodiment of a fastener.

Depicted in FIG. 29 is another alternative embodiment of a fastener 290. Fastener 290 comprises a backspan 292 and arms 294, 296. Fastener 290 included a thickness 297 that is generally consistent through backspan 292 and anus 294, 296. Arms 294, 296 further include tips 298, 300, each tip 298, 300 having an internal cleat 302 having a cleat base 304. Arms 294, 296 in combination with internal cleat 302 and cleat base 304 define a durable tissue retention zone 306 to capture elastic tissue using the through-and-through insertion method as previously described.

Figure 30:
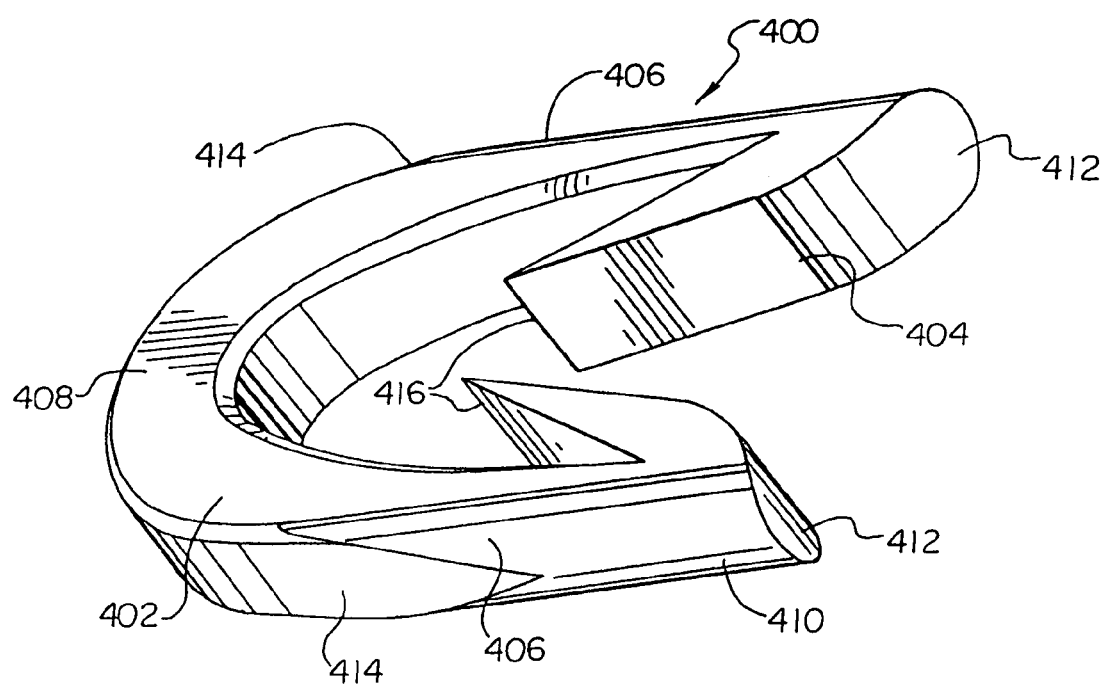
FIG. 30 is a perspective view of an embodiment of a fastener.
Figure 31:
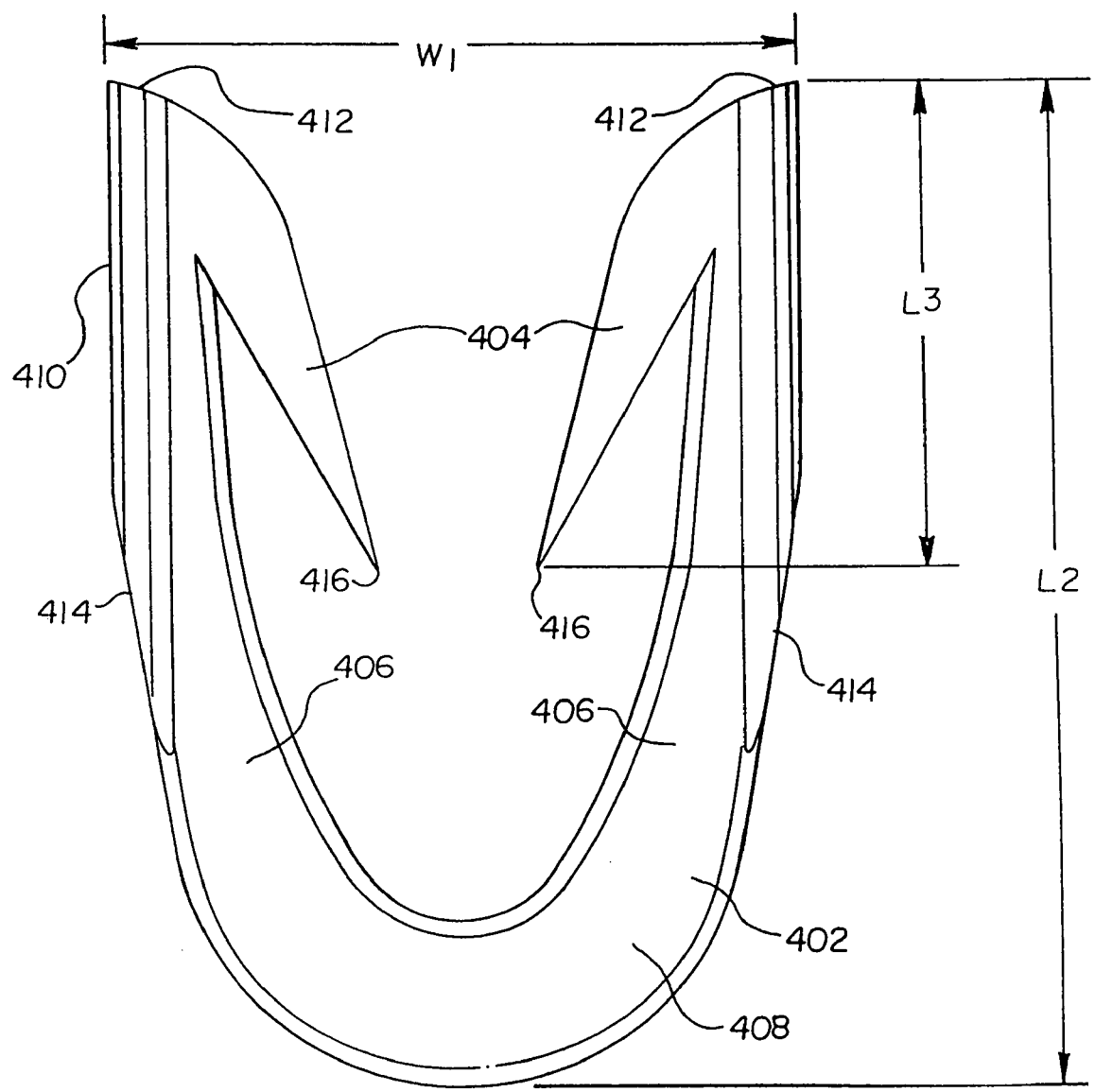
FIG. 31 is a top view of the fastener of FIG. 30.

In FIGS. 30 and 31, there is shown an earlier embodiment of a fastener 400 of the present invention. Fastener 400 has body portion 402, which comprises a cross-member 408 connecting a pair of fork members or legs 406. The outer margins 410 of each leg 406 are dimensioned and shaped accommodatingly to the retaining space 186 of piercing members 174, 176, allowing fastener 400 to fit and slide between the piercing members 174, 176. Shoulders 414 preferably are provided to engage the solid cylindrical cross-section of the backspan member 190, thus allowing fastener 400 to be advanced distally wit motion of the piercing members 174, 176. The distal end 412 of each leg 406 is incurvately shaped to allow easier passage through an opening in skin, referred to as a skive, that is created by piercing members 174, 176. Inwardly directed barbs 404 preferably are provided on each leg 406 to resist withdrawal of the fastener once emplaced.

Although an overall U-shape for the fastener 400, as shown in FIGS. 30 and 31 is preferred, other shapes having a capability for bilateral tissue engagement are also possible, and within the scope of the invention. Such other shapes include for example, but are not limited to, a square shape similar to an ordinary staple, a semi-circular or C-shape era V-shape or W-shape, in which the cross-member 408 has bends or other features. While the shape of fastener 400 is generally determined in a planar configuration, it will be recognized that other non-planar shapes and configurations can be used, such as a fastener having multiple projections for each leg 406, with each projection oriented in a different plane, or a fastener having cross-member 408 arranged in a V-shape projecting out of the normal plane of the fastener 400. Two leg members 406 are preferred, but it will be understood that additional leg members 406 could be aided in the same or a different plane of the fastener 400 such that the leg members of each side of the fastener form a dident or trident configuration, for example.

Figure 32:
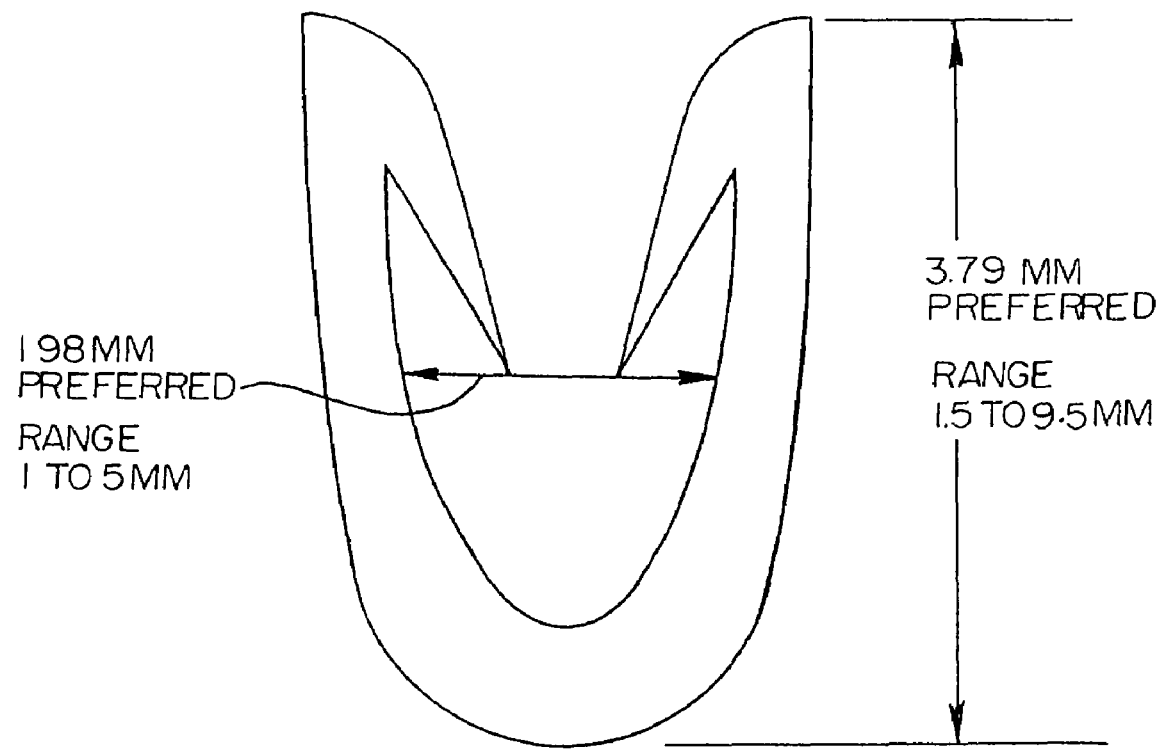
FIG. 32 is a top view of the fastener of FIG. 30.

As shown in FIG. 32, an inner cross-sectional area 409 is defined by the fastener 400 for capturing the compressed dermal tissue. In a preferred embodiment, inner cross-sectional area 409 ranges from 1.5 sq. mm to 50 sq. mm and most preferably about 5 sq. mm to 10 sq. mm. This area is generally defined by an inner diameter length of between 1.5 mm and 9 mm and most preferably about 3.8 mm and an inner diameter width of between 1 mm and 5 mm and most preferably about 2 mm. It will be apparent that numerous shapes and configurations can be used for the shape and arrangement of cross-sectional area 409. Preferably, inner cross-sectional area 409 is generally arrowhead shaped as a result of the positioning of the barbs 412. As will be described, the barbs 412 or similar anti-reversing projections resist against the withdrawal of fastener 400. While the barbs 412 are preferably oriented into the inner cross-sectional area 409, it will be appreciated that barbs 412 may be omitted or may be oriented outwardly.

Although it is possible for fastener 400 to be deformed during delivery and application, preferably the majority of dermal tissue retained within cross-sectional area 409 is captured in a compressed state by a fastener 400 that is sufficiently rigid so as to retain the dimensional integrity of cross-sectional area 409 within +/−30% of its designed area for a period of preferably at least 10 days. Most preferably, structural integrity of fastener 400 is maintained for at least 21 days. In this way, the dermal tissue captured in fastener 400 is retained in a compressed state for a period sufficient to allow the biological healing process to occur without the dermal tissue being under tension during the healing process. Preferably, the dimensions of the fastener 400 and the operation of the applicator assembly 100 coordinate to create a compression ratio of dermal tissue within the inner cross-sectional area 409 that is greater than one. The compression ratio is defined either as a ratio of area or a ratio of width. In the case of width, the compression ratio is the ratio of the dimension defined by the position of the skive relative to the vertical interface 51 when the dermal tissue is at rest divided by the position of the skive relative to the vertical interface as held by the fastener 400. In the case of area, the compression ratio is the ratio of the area of dermal tissue that will be retained by the fastener 400 when that dermal tissue is at rest divided by the actual cross-sectional area 409.

Alternatively, it is possible to take advantage of the bilateral tissue fastening in the tissue target zone as taught by the present invention with a deformable fastener where the deforming of a bioresorbable or bioabsorbable fastener serves to provide at least some of the compression of the dermal tissue such that the need for a mechanical tissue manipulator is reduced or potentially eliminated. In this embodiment, a bioresorbable or bioabsorbable fastener would be deformed by the applicator apparatus in order to appropriately compress the dermal tissue. Deformation of a bioresorbable or bioabsorbable fastener could be accomplished in a number of ways, including prestressing the fastener into an open configuration such that it returns to a closed configuration, with or without mechanical assistance from the applicator, application of ultrasound, heat or light energy to alter the shape of, or reduce or relax stresses in, the fastener in situ, designing a polymer material with appropriate shapes and compositions that the material is deformable upon deployment without fracturing, or any combination of these techniques.

Fastener 400 is preferably formed from any suitable biodegradable material. The currently most preferred biodegradable material is a lactide/glycolide copolymer where the ratio is never less than at least 10% of one element and preferably in a range of 60%–70% lactide. Examples of other suitable materials include poly(dl-lactide), poly(l-lactide), polyglycolide, poly(dioxanone), poly(glycolide-co-trimethylene carbonate), poly(l-lactide-co-glycolide), poly(dl-lactide-co-glycolide), poly(l-lactide-co-dl-lactide) and poly(glycolide-co-trimethylene carbonate-co-dioxanone). In addition, other suitable materials could include compositions with naturally occurring biopolymers such as collagen and elastin, or stainless steel, metal, nylon or any other biocompatible materials in the case of a non-absorbable fastener, or even various combinations of such materials depending upon the desired application and performance of the fastener.

While a preferred embodiment of a dynamic, bioabsorbable fastener of the present invention has been described, it will be apparent to one skilled in the art that a fastener in accordance with the present invention is capable of numerous other embodiments without departing from the scope and spirit of the present invention.

What is claimed is:

1. A dynamic bioabsorbable staple for use with a wound in living human tissue having opposed sides, the staple comprising:
   a bioabsorbable staple body including a pair of staple arms operably joined at a shoulder portion by a backspan, each arm further including an elbow portion having an inwardly projecting cleat, the staple arms, the inwardly projecting cleats and the backspan defining an internal tissue capture zone; and
   each shoulder portion including an interior shoulder angle generally defined by the backspan and the staple arm, the shoulder portion constructed so that the interior shoulder angle is between 70°–100° in a first position at an insertion time, the interior shoulder angle transitioning to between 120°–180° in a second deformed position at a second time subsequent to the insertion time in response to lateral forces naturally exerted by the opposed sides of the wound and deformation of at least the shoulder portions of the bioabsorbable staple body caused by polymeric creep and adsorption of the bioabsorbable staple body in the living human tissue.

2. The staple of claim 1, wherein each elbow portion includes an interior elbow angle generally defined by the staple arm and the cleat, the elbow portion constructed so that the interior elbow angle is less than 70° in the first inserted position at the insertion time, the interior elbow angle transitioning to a maximum of 90° in the second deformed disposition at the second time.

3. The staple of claim 1, wherein the second time is not less than 12 hours subsequent to the insertion time.

4. A dynamic bioabsorbable staple for joining living tissue, comprising:
   a staple body made of a bioabsorbable material including a pair of staple arms operably joined by a backspan, each staple arm including:
   means for dynamically transitioning the staple arm over a range of positions from an initial deployed position to a subsequent deformed position in response to forces exerted by living tissue on the staple arm after deployment of the staple body in living tissue; and
   means for retaining tissue throughout the range of positions and longer than a minimum degradation period of the bioabsorbable material in living tissue.

5. The dynamic bioabsorbable staple of claim 4, wherein the means for retaining tissue comprises a rounded cleat projecting inwardly into a tissue capture area defined by the staple arms, the backspan and the rounded cleat of each staple arm.

6. The dynamic bioabsorbable staple of claim 4, wherein the means for dynamically transitioning defines an interior shoulder angle of between about 70–100° when the staple body is in the initial deployed position.

7. The dynamic bioabsorbable staple of claim 4, wherein the means for dynamically transitioning defines an interior shoulder angle of between about 120–180° when the staple body is in the subsequent deformed position.

8. The dynamic bioabsorbable staple of claim 4, wherein the initial deployed position has a minimum dry initial closure strength of about 1.2 $lb_F$.

9. The dynamic bioabsorbable staple of claim 4, wherein the means for retaining includes means for presenting a maximum insertion width of the means for retaining tissue that is greater than a width of a pierced opening in living tissue through which the staple arm is deployed.

10. The dynamic bioabsorbable staple of claim 9, wherein the means for presenting a maximum insertion width functions to cause at least a portion of living tissue surrounding the pierced opening to be stretched over and elastically retained by the means for retaining tissue for longer than the minimum degradation period of the bioabsorable material in living tissue.

11. The dynamic bioabsorbable staple of claim 4, wherein the bioabsorbable material comprises a blended bioabsorbable copolymer.

* * * * *

UNITED STATES PATENT AND TRADEMARK OFFICE
Certificate

Patent No. 7,112,214 B2

Patented: September 26, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: James A. Peterson, Edina, MN (US); Christopher J. Sperry, Plymouth, MN (US); Joseph M. Gryskiewicz, Edina, MN (US); Delmer L. Smith, Edina, MN (US); and David B. Herridge, Mendota Heights, MN (US).

Signed and Sealed this Tenth Day of April 2012.

GARY JACKSON
*Supervisory Patent Examiner*
Art Unit 3734
Technology Center 3700